(12) United States Patent
Chin

(10) Patent No.: US 7,214,180 B2
(45) Date of Patent: May 8, 2007

(54) METHOD FOR CARDIAC RESTRAINT

(75) Inventor: Albert K Chin, Palo Alto, CA (US)

(73) Assignee: Origin Medsystems, Inc., Santa Clara, CA (US)

(*) Notice: Subject to any disclaimer, the term of this patent is extended or adjusted under 35 U.S.C. 154(b) by 220 days.

(21) Appl. No.: 10/338,163

(22) Filed: Jan. 6, 2003

(65) Prior Publication Data
US 2006/0229490 A1    Oct. 12, 2006

Related U.S. Application Data

(63) Continuation of application No. 09/779,715, filed on Feb. 8, 2001, now Pat. No. 6,569,082, which is a continuation-in-part of application No. 09/635,345, filed on Aug. 9, 2000.

(60) Provisional application No. 60/150,737, filed on Aug. 25, 1999, provisional application No. 60/148,130, filed on Aug. 10, 1999.

(51) Int. Cl.
*A61F 13/00* (2006.01)
(52) U.S. Cl. ........................................ 600/37
(58) Field of Classification Search ............ 600/37, 600/16–18; 606/139, 148; 623/2.1, 2.11; 607/129
See application file for complete search history.

(56) References Cited
U.S. PATENT DOCUMENTS
207,932 A    9/1878 Alvord
(Continued)

FOREIGN PATENT DOCUMENTS
DE    39 42 589    12/1989
(Continued)

OTHER PUBLICATIONS

Kirklin, John W., et al., "Cardiac Surgery: Morphology, Diagnostic Criteria, Natural History, Techniques, Results, and Indications", vol. 2, Second Edition, 1993, Chapter 52, p. 1695.
(Continued)

*Primary Examiner*—John P. Lacyk
(74) *Attorney, Agent, or Firm*—Fenwick & West LLP

(57) ABSTRACT

Apparatus and methods for using the apparatus are disclosed for cardiac restraint. More specifically, the apparatus and methods are directed to accessing the pericardium, accessing the heart within the pericardium, and restraining the heart by at least partially enclosing the heart with the apparatus. An embodiment of a cardiac restraint apparatus according to the present invention comprises a jacket, the jacket having a rim which defines an opening for receiving a heart. The apparatus also comprises a knot pusher that has a hollow elongate body, as well as a strand that extends around the rim of the jacket and is tied into a slipknot. The strand is positioned such that at least one end portion of the strand extends through the knot pusher such that a distal end of the knot pusher can be moved into engagement with the slipknot, whereby pulling the end portion of the strand away from the heart while pushing the knot pusher against the slipknot and reducing the diameter of the opening defined by the rim. In addition, the apparatus comprises one or more guide elements that are attached to the jacket.

7 Claims, 13 Drawing Sheets

U.S. PATENT DOCUMENTS

| | | |
|---|---|---|
| 702,789 A | 6/1902 | Gibson |
| 1,727,495 A | 9/1929 | Wappler |
| 1,867,624 A | 7/1932 | Hoffman |
| 2,011,169 A | 8/1935 | Wappler |
| 2,028,635 A | 1/1936 | Wappler |
| 2,316,297 A | 4/1943 | Southerland et al. |
| 2,868,206 A | 1/1959 | Stoesser |
| 2,944,552 A | 7/1960 | Cannon |
| 3,185,155 A | 5/1965 | Slaten et al. |
| 3,336,916 A | 8/1967 | Edlich |
| 3,357,433 A | 12/1967 | Fourestier et al. |
| 3,856,016 A | 12/1974 | Davis |
| 3,870,048 A | 3/1975 | Yoon |
| 3,882,854 A | 5/1975 | Hulka et al. |
| 3,920,024 A | 11/1975 | Bowers |
| 3,934,115 A | 1/1976 | Peterson |
| RE29,088 E | 12/1976 | Shaw |
| 4,022,191 A | 5/1977 | Jamshidi |
| 4,181,123 A | 1/1980 | Crosby |
| 4,235,246 A | 11/1980 | Weiss |
| 4,270,549 A | 6/1981 | Heilman |
| 4,271,839 A | 6/1981 | Fogarty et al. |
| 4,291,707 A | 9/1981 | Heilman et al. |
| 4,318,410 A | 3/1982 | Chin |
| 4,319,562 A | 3/1982 | Crosby |
| 4,479,497 A | 10/1984 | Fogarty et al. |
| 4,493,711 A | 1/1985 | Chin et al. |
| 4,526,175 A | 7/1985 | Chin et al. |
| 4,630,609 A | 12/1986 | Chin |
| 4,662,371 A | 5/1987 | Whipple et al. |
| 4,765,341 A | 8/1988 | Mower et al. |
| 4,779,611 A | 10/1988 | Grooters et al. |
| 4,784,133 A | 11/1988 | Mackin |
| 4,863,440 A | 9/1989 | Chin |
| 4,921,483 A | 5/1990 | Wijay et al. |
| 4,957,477 A | 9/1990 | Lundback |
| 4,991,578 A | 2/1991 | Cohen |
| 5,033,477 A * | 7/1991 | Chin et al. .................. 607/131 |
| 5,071,428 A | 12/1991 | Chin et al. |
| 5,129,394 A | 7/1992 | Mehra |
| 5,131,905 A | 7/1992 | Grooters |
| 5,143,082 A | 9/1992 | Kindberg et al. |
| 5,150,706 A | 9/1992 | Cox et al. |
| 5,163,949 A | 11/1992 | Bonutti |
| 5,183,464 A | 2/1993 | Dubrul et al. |
| 5,215,521 A | 6/1993 | Cochran et al. |
| 5,246,014 A | 9/1993 | Williams et al. |
| 5,256,132 A | 10/1993 | Snyders |
| 5,271,380 A | 12/1993 | Riek et al. |
| 5,318,589 A | 6/1994 | Lichtman |
| 5,331,975 A | 7/1994 | Bonutti |
| 5,334,150 A | 8/1994 | Kaali |
| 5,336,252 A | 8/1994 | Cohen |
| 5,339,801 A | 8/1994 | Poloyko et al. |
| 5,373,840 A | 12/1994 | Knighton |
| 5,376,076 A | 12/1994 | Kaali |
| 5,385,156 A | 1/1995 | Oliva |
| 5,391,156 A | 2/1995 | Hildwein et al. |
| 5,433,198 A | 7/1995 | Desai |
| 5,437,680 A | 8/1995 | Yoon |
| 5,464,447 A | 11/1995 | Fogarty et al. |
| 5,482,925 A | 1/1996 | Hutsell |
| 5,496,345 A | 3/1996 | Kieturakis et al. |
| 5,514,153 A | 5/1996 | Bonutti |
| 5,540,711 A | 7/1996 | Kieturakis et al. |
| 5,551,947 A | 9/1996 | Kaali |
| 5,569,183 A | 10/1996 | Kieturakis |
| 5,569,291 A | 10/1996 | Privitera et al. |
| 5,569,292 A | 10/1996 | Scwemberger et al. |
| 5,571,161 A | 11/1996 | Starksen |
| 5,591,192 A | 1/1997 | Privitera et al. |
| 5,601,576 A | 2/1997 | Garrison |
| 5,601,589 A | 2/1997 | Fogarty et al. |
| 5,607,441 A | 3/1997 | Sierocuk et al. |
| 5,613,937 A | 3/1997 | Garrison et al. |
| 5,613,947 A | 3/1997 | Chin |
| 5,618,287 A | 4/1997 | Fogarty et al. |
| 5,634,895 A | 6/1997 | Igo et al. |
| 5,650,447 A | 7/1997 | Keefer et al. |
| 5,653,722 A | 8/1997 | Kieturakis |
| 5,653,726 A | 8/1997 | Kieturakis |
| 5,667,520 A | 9/1997 | Bonutti |
| 5,669,927 A | 9/1997 | Boebel et al. |
| 5,681,278 A | 10/1997 | Igo et al. |
| 5,685,820 A | 11/1997 | Riek et al. |
| 5,690,648 A | 11/1997 | Fogarty et al. |
| 5,695,504 A | 12/1997 | Gifford, III et al. |
| 5,702,343 A | 12/1997 | Alferness |
| 5,702,417 A | 12/1997 | Hermann |
| 5,707,390 A | 1/1998 | Bonutti |
| 5,713,950 A | 2/1998 | Cox |
| 5,716,392 A | 2/1998 | Bourgeois et al. |
| 5,722,977 A | 3/1998 | Wilhelmy |
| 5,725,492 A | 3/1998 | Igo et al. |
| 5,728,148 A | 3/1998 | Bostrom et al. |
| 5,730,756 A | 3/1998 | Kieturakls |
| 5,738,628 A | 4/1998 | Sierocuk et al. |
| 5,755,764 A | 5/1998 | Schroeppel |
| 5,755,765 A | 5/1998 | Hyde et al. |
| 5,762,604 A | 6/1998 | Kieturakis |
| 5,772,680 A | 6/1998 | Kieturakls et al. |
| 5,797,946 A | 8/1998 | Chin |
| 5,800,449 A | 9/1998 | Wales |
| 5,810,878 A | 9/1998 | Burel et al. |
| 5,827,216 A | 10/1998 | Igo et al. |
| 5,860,997 A | 1/1999 | Bonutti |
| 5,897,586 A | 4/1999 | Molina |
| 5,900,433 A | 5/1999 | Igo et al. |
| 5,902,331 A | 5/1999 | Bonner et al. |
| 5,904,711 A | 5/1999 | Flom et al. |
| 5,931,810 A | 8/1999 | Grabek |
| 5,957,835 A | 9/1999 | Anderson et al. |
| 5,957,880 A | 9/1999 | Igo et al. |
| 5,972,010 A | 10/1999 | Taheri |
| 5,972,013 A | 10/1999 | Schmidt |
| 5,972,020 A | 10/1999 | Carpentier et al. |
| 5,980,548 A | 11/1999 | Evans et al. |
| 6,007,546 A | 12/1999 | Snow et al. |
| 6,010,531 A * | 1/2000 | Donlon et al. ............... 623/2.1 |
| 6,030,406 A | 2/2000 | Davis et al. |
| 6,036,714 A | 3/2000 | Chin |
| 6,039,748 A | 3/2000 | Savage et al. |
| 6,077,218 A | 6/2000 | Alferness |
| 6,080,174 A | 6/2000 | Dubrul et al. |
| 6,085,754 A | 7/2000 | Alferness et al. |
| 6,095,968 A | 8/2000 | Snyders |
| 6,096,064 A | 8/2000 | Routh |
| 6,102,046 A | 8/2000 | Weinstein et al. |
| 6,126,590 A * | 10/2000 | Alferness ..................... 600/37 |
| 6,132,456 A | 10/2000 | Sommer et al. |
| 6,156,009 A | 12/2000 | Grabek |
| 6,162,195 A | 12/2000 | Igo et al. |
| 6,165,183 A | 12/2000 | Kuehn et al. |
| 6,206,004 B1 | 3/2001 | Schmidt et al. |
| 6,237,605 B1 | 5/2001 | Vaska et al. |
| 6,267,763 B1 | 7/2001 | Castro |
| 6,287,250 B1 | 9/2001 | Peng et al. |
| 6,322,536 B1 | 11/2001 | Rosengart et al. |
| 6,346,074 B1 | 2/2002 | Roth |
| 6,428,556 B1 | 8/2002 | Chin |
| 6,463,332 B1 * | 10/2002 | Aldrich ..................... 607/101 |
| 6,478,028 B1 | 11/2002 | Paolitto et al. |
| 6,488,689 B1 | 12/2002 | Kaplan et al. |
| 6,569,082 B1 | 5/2003 | Chin |

| | | | |
|---|---|---|---|
| 6,607,547 B1 | 8/2003 | Chin | |
| 6,612,978 B2* | 9/2003 | Lau et al. | 600/37 |
| 6,689,048 B2* | 2/2004 | Vanden Hoek et al. | 600/37 |
| 6,697,677 B2 | 2/2004 | Dahl et al. | |
| 6,702,732 B1* | 3/2004 | Lau et al. | 600/37 |
| 6,706,052 B1 | 3/2004 | Chin | |
| 6,835,193 B2 | 12/2004 | Epstein et al. | |
| 6,889,091 B2 | 5/2005 | Hine et al. | |
| 2002/0035361 A1 | 3/2002 | Houser et al. | |
| 2002/0052602 A1 | 5/2002 | Wang et al. | |
| 2002/0058925 A1 | 5/2002 | Kaplan et al. | |
| 2002/0111637 A1 | 8/2002 | Kaplan et al. | |
| 2002/0173622 A1 | 11/2002 | Wettstein et al. | |
| 2002/0177207 A1 | 11/2002 | Sugiyama et al. | |
| 2003/0212446 A1 | 11/2003 | Kaplan et al. | |

FOREIGN PATENT DOCUMENTS

| | | |
|---|---|---|
| EP | 0095727 A1 | 12/1983 |
| EP | 0 642 764 | 9/1994 |
| EP | 0791330 A2 | 8/1997 |
| FR | 1 370580 | 8/1964 |
| GB | 2 082 459 | 8/1981 |
| GB | 2 195 540 | 9/1987 |
| SU | 510235 | 4/1976 |
| SU | 1371689 | 3/1986 |
| WO | WO 96/00038 | 1/1996 |
| WO | WO 96/32882 | 10/1996 |
| WO | WO97/26831 | 7/1997 |
| WO | WO 98/24378 | 6/1998 |
| WO | WO 98/24488 A2 | 6/1998 |
| WO | WO 98/24488 A3 | 6/1998 |
| WO | WO 99/13785 | 3/1999 |
| WO | WO 99/13936 | 3/1999 |

OTHER PUBLICATIONS

Sabiston, David C., Jr., et al., "Atlas of Cardiothoracic Surgery", W.B. Saunders Company, 1995, pp. 235-237.
Grandjean, Jan G., et al., "Coronary Reoperation via Small Laparotomy Using Right Gastroepiploic Artery Without CPB", Society of Thoracic Surgeons, 1996, pp.
Benetti, Federico, et al., "Video Assisted Coronary Bypass Surgery", J Card Surgery, 1995, pp. 620-625.
S. Bartoccioni, et al., Laparoscopic Harvesting of Right Gastroepiploic Artery for Coronary Artery Bypass Graft Performed Without Sternotomy [online], [retrieved on Oct. 5, 1999] Retrieved from the internet <URL:http://www.ctsnet.org/doc/2628.
Spodick, David H., "IPTD: Intrapericardial Therapeutics and Diagnostics: The PerDUCER Permits Direct Access to the Heart", Cath-Lab Digest, Sep. 1999, vol. 7, No. 9.
Simonsen, Michael, Ph.D., "Researchers Undaunted by Setbacks in the Angiogenesis Sector", American Health Consultants, vol. 5, No. 5, May 1999.
Kaminski, Diane, "Firm Aims to Bypass Heart-piercing Treatments", Medical Industry Today, Medical Data International, Sep. 23, 1998.
Spodick, David H., "Directly Applied Cardiac Therapy: Experts Explore Potential Benefits", Internal Medicine World Report, 1998.
Comedicus Gets Approval to Sell Product in European Union, Mar. 1, 1999, Swenson NHB Investor Relations.
Comedicus Incorporated, Update—Oct. 1999; Equity Investment Information Sheet, May 17, 1999.
The 4th International Symposium on Intrapericardial Therapeutics and Diagnostics, Mar. 6, 1999, New Orleans, Louisiana.
Dimitri, W.R., et al., "A Quick and Atraumatic Method of Autologous Vein Harvesting Using the Subcutaneous Extraluminal Dissector", J. Cardiovasc. Surg., 28:103-11, 1987.
Broadman, R. et al., "ICD Implantation via Thoracoscopy, "Mailslot" Thoracotomy, and Subxiphoid Incision," The Annals of Thoracic Surgery, vol. 57, No. 2, Feb. 1994, pp. 475-476.

Carpentier, A., "Technique d'implantation de pace-maker par une voie d'abord abdominale sous-xyphoidienne," La Presse Medicale, Masson et Cie, Editeurs, Paris, vol. 76, No. 2, Jan. 13, 1968, 2 pp.
Comedicus Incorporated, Equity Investment Information Sheet, May 17, 1999.
De Feyter, P.J. et al., "Permanent Cardiac Pacing with Sutureless Myocardial Electrodes: Experience in First One Hundred Patients," PACE, vol. 3, No. 2, Mar. 1980, pp. 144-149.
Delaria, G.A. et al., "Leg Wound Complications Associated With Coronary Revascularization", J. Thorac, Cardiovasc. Surgery, 81:403-407, 1981.
Dimitri, W.R., et al., "A Quick and Atraumatic Method of Autologous Vein Harvesting Using the Subcutaneous Extraluminal Dissector", J. Cardiovasc. Surg., 28:103-11, 1987.
Fogarty, M.D., Thomas J., et al., "Selected Applications of Balloon Dissection", pp. 45-52.
Fontenelle, Larry, J., "Subxiphoid Pericardial Window", Thoracic and Cardiovascular Surgery, The American Association for Thoracic Surgery, Jul. 1971, vol. 62, No. 1, pp. 95-97.
Hauer, G., et al. "Endoscopic Subfascial Discussion of Perforating Vein", Surg. Endos. 2:5-12. 1988.
"Incision Decision", Atrium Medical Corporation advertisement, appearing in J. Thorac. Cardiovasc. Surg., 83(4). 1982.
Levin, Bradley H., "The Subxiphoid Pericardial Window", Surgery, Gynecology & Obstetrics, Dec. 1982, vol. 155, pp. 804-806.
Meldrum-Hanna, W. et al., "Long Saphenous Vein Harvesting," J. Surg., 56:923-924, 1986.
Moazami, N., M.D. et al., "Minimatly Invasive Greater Saphenous Vein Harvesting For Coronary Artery Bypass Surgery", Mar. 1997, pp. 94-98.
Prager, Richard L., et al., "The Subxiphoid Approach to Pericardial Disease", The Annals of Thoracic Surgery, vol. 34, No. 1, Jul. 1982.
Rashid, A., et al., "Subcutaneous Technique for Saphenous Vein Harvest", Ann. Thorac. Surg., 37(2):169-170. 1984.
Santos, Gil H., et al., "The Subxiphoid Approach in the Treatment of Pericardial Effusion", Albert Einstein College of Medicine, Sep. 21, 1976, pp.467-470.
"Saphenous Vein Grafts Are No. 1. Period", Atrium Medical Corporation advertisement, appearing in J. Thorac. Cardiovas. Surg., 82(6), 1981.
Stewart, S., M.D., "Placement of the Sutureless Epicardial Pacemaker Lead by the Subxiphoid Approach," The Annals of Thoracic Surgery, vol. 18, No. 3, Sep. 1974, pp. 308-313.
Watkins, Jr., L., M.D. et al., "Implantation of the Automatic Defibrillator: The Subxiphold Approach," The Annals of Thoracic Surgery, vol. 34, No. 5, Nov. 1982, pp. 515-520.
Wheatley, D.J., M.D., ed., "Surgery of Coronary Artery Disease", C.V. Mosby Company, pp. 348-349, pp. 374-375.
Zentati M., M.D. et al., "Left Heart Pacing Lead Implantation Using Subxiphoid Videopericardloscopy," J. Cardiovasc Electrophysiol, vol. 14, Sep. 2003, pp. 949-963.
International Search Report and Written Opinion, PCT/US04/00859, Jun. 20, 2005.
International Search Report and Written Opinion, PCT/US04/00859, Jun 20, 2005.
International Search Report and Written Opinion, PCT/US04/00760, Jul. 6, 2005.
Myers, E. L. et al., "Tsg101, an Inactive Homologue of Ubiquitin Ligase E2, Interacts Specifically With Human Immunodeficiency Virus Type 2 Gag Polyprotein and Results in Increased Levels of Ubiquianted Gag," J. Virol, Nov. 2002, vol. 76, No. 22.
PCT International Search Report and Written Opinion; PCT/US04/34538, Nov. 3, 2005, 10 pages.
PCT International Search Report and Written Opinion, PCT/US04/00760, Sep. 27, 2006, 7 pages.

* cited by examiner

METHOD FOR CARDIAC RESTRAINT

CROSS-REFERENCE TO RELATED APPLICATIONS

This application is a continuation of application Ser. No. 09/779,715, filed Feb. 8, 2001, by Albert K. Chin, entitled "Apparatus and Method for Cardiac Restraint", now issued as U.S. Pat. No. 6,569,082, which application is a continuation in part of pending application Ser. No. 09/635,345, filed Aug. 9, 2000, by Albert K. Chin, entitled "Apparatus and Method for Subxiphoid Endoscopic Access", which applications are incorporated herein in the entireties by this reference thereto which claims benefit of Ser. No. 60/148,130 filed Aug. 10, 1999, and claims benefit of Ser. No. 60/150,737 filed Aug. 25, 1999.

BACKGROUND OF THE INVENTION

1. Field of the Invention

The present invention relates to apparatus and methods for restraining the heart. More particularly, the invention relates to apparatus and methods for accessing the pericardium and at least partially enclosing the heart with a cardiac restraint apparatus.

2. Description of the Related Art

The present invention is generally directed to apparatus and methods for restraint of the cardiac wall. The invention is particularly suited for the treatment of cardiac diseases which result in atrial or ventricular dilation. The invention includes minimally invasive methods to access the heart and restrain the cardiac wall, resulting in the prevention or reduction of cardiac dilation in patients known to have experienced such dilation or who have a predisposition for such dilation occurring in the future. A cardiac restraint apparatus according to the present invention is typically applied to the epicardial surface of the heart, such that the cardiac restraint apparatus at least partially enclosed the heart.

Cardiac dilation occurs with different forms of cardiac disease, including congestive heart disease, post-myocardial infarctions, and dilated cardiomyopathy. In certain instances, congestive heart disease may result from viral infections. In such cases, the heart may enlarge to such an extent that the adverse consequences of heart enlargement continue after the viral infection has passed and the disease continues its progressively debilitating course. In some cases, such as post-myocardial infarction, the dilation may be localized to only a portion of the heart. In other cases, such as hypertrophic cardiomyopathy, there is typically increased resistance to filling of the left ventricle with concomitant dilation of the left atria. In dilated cardiomyopathy, the dilation is typically of the left ventricle with resultant failure of the heart as a pump. In advanced cases, dilated cardiomyopathy involves the majority of the heart. Causes of congestive heart disease are not fully known.

As the heart enlarges, the heart is performing an increasing amount of work in order to pump blood during each heart beat. In time, the heart becomes so enlarged that the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood. With each type of cardiac dilation, there are associated problems ranging from arrhythmias which arise due to the stretch of myocardial cells, to leakage of the cardiac valves due to enlargement of the valvular annulus.

Drugs are sometimes employed to assist in treating problems associated with cardiac dilation. For example, Digoxin increases the contractility of the cardiac muscle and thereby causes enhanced emptying of the dilated cardiac chambers. On the other hand, some drugs, for example, beta-blocking drugs, decrease the contractility of the heart and thus increase the likelihood of dilation. Other drugs including angiotensin-converting enzyme inhibitors such as Enalopril, which help to reduce the tendency of the heart to dilate under the increased diastolic pressure experienced when the contractility of the heart muscle decreases. Many of these drugs, however, have side effects which make them undesirable for long-term use.

Apparatus to prevent or reduce dilation and thereby reduce the consequences of dilation have also been described. Patches made from low porosity materials, for example Dacron™, have been used to support the cardiac wall. Other apparatus are found in U.S. Pat. No. 4,957,477 to Lundback dated Sep. 18, 1990; U.S. Pat. No. 5,131,905 to Grooters dated Jul. 21, 1992; U.S. Pat. No. 5,150,706 to Cox et al. dated Sep. 29, 1992; U.S. Pat. No. 5,143,082 to Kindberg et al dated Sep. 1, 1992; U.S. Pat. No. 5,256,132 to Snyders dated Oct. 26, 1993; U.S. Pat. No. 5,702,343 to Alferness dated Dec. 30, 1997; U.S. Pat. No. 6,077,218 to Alferness dated Jun. 20, 2000; U.S. Pat. No. 6,085,754 to Alferness dated Jul. 11, 2000; and U.S. Pat. No. 6,095,968 to Snyders dated Aug. 1, 2000.

The '477 patent teaches a double-walled jacket surrounding the heart. A fluid fills a chamber between the walls of the jacket. The inner wall is positioned against the heart and is pliable to move with the heart. Movement of the heart during beating displaces fluid within the jacket chamber. The '706 patent discloses a medical apparatus for enclosing an internal body organ, comprising a filamentary strand with noose and free end portions and a surgical bag with an opening. The '082 patent discloses a cooling net for cardiac or transplant surgery, comprising a porous net that is fitted and secured around the organ. Both of the '905 and '132 patents teach cardiac assist apparatus which pump fluid into chambers opposing the heart to assist systolic contractions of the heart. The '343 and '218 patents teach an adjustable jacket to constrain cardiac expansion during diastole. The '754 patent discloses a biologically compatible jacket adapted to be secured to the heart. The '968 patent discloses a viscous cardioplasty jacket for buttressing the ventricular heart walls.

None of these apparatus include a sheath to facilitate endoscopic introduction of the apparatus, or guide elements for positioning the cardiac restraint apparatus around the heart. Moreover, none of these apparatus include hollow guide tubes that permit an instrument to be advanced through their lumens to engage the mouth of the jacket and secure the mouth of the jacket to the pericardium. Furthermore, none of these references teach the introduction of a cardiac restraint apparatus via a single subxiphoid incision. Accordingly, there is a need for an improved cardiac restraint apparatus that can be more easily introduced via a minimally invasive approach, and improved minimally invasive methods for introducing cardiac restraint apparatus.

SUMMARY OF THE INVENTION

The invention is a method and apparatus for accessing the heart within the pericardium and restraining the heart by at least partially enclosing the heart with a cardiac restraint apparatus.

One embodiment of a cardiac restraint apparatus according to the invention comprises a jacket, the jacket having a rim which defines an opening for receiving a heart. The apparatus also comprises a knot pusher that has a hollow elongate body, and a strand that extends around the rim of the jacket and is tied into a slipknot. The strand is positioned such that at least one end portion of the strand extends through the knot pusher such that a distal end of the knot pusher can be moved into engagement with the slipknot, whereby pulling the end portion of the strand away from the heart while pushing the knot pusher against the slipknot and reducing the diameter of the opening defined by the rim. In addition, the apparatus comprises one or more guide elements that are attached to the jacket.

In another embodiment of a cardiac restraint apparatus according to the invention, the jacket is folded to reduce the profile of the apparatus. Optionally, the folded jacket is enclosed by a sheath. One embodiment of such a sheath includes a generally cylindrical body having a proximal end and a distal end, and also includes perforations along the sheath body such that the sheath can be removed from the apparatus by tearing the sheath body along the perforations. Optionally, a pull tab is attached to the proximal end of the sheath body. By pulling the pull tab away from the jacket, the surgeon can tear the sheath along the perforations and remove the torn sheath from the patient.

In one embodiment of a cardiac restraint apparatus according to the invention, the strand extending around the rim of the jacket is a suture strand, for example a nylon suture strand.

In a class of embodiments the guide elements are one or more guide tubes removably attached to the rim of the jacket. In some of these embodiments, the guide tubes are hollow. In some of the embodiments, at least one of the guide tubes defines a lumen dimensioned to receive a surgical instrument, for example a tacking instrument. In other embodiments, the guide elements are one or more handles, for example handles composed of suture strands, attached to the rim of the jacket.

In another class of embodiments, the apparatus comprises at least one elastic band having a first portion terminating at a first end and a second portion terminating at a second end, with the first portion and the second portion of the elastic band being joined together at a location between the first end and the second end. The apparatus also includes a sheath, which includes a generally cylindrical body having a proximal end and a distal end. The sheath body may also define perforations, preferably longitudinally positioned perforations, such that the sheath can be removed from the apparatus by tearing the body along the perforations. The sheath can also include a pull tab that is attached to the proximal end of the sheath body, for pulling the sheath away from the apparatus by pulling the pull tab away from the jacket.

In some such embodiments, the elastic band includes calibrated markings for calibrating the tension of the elastic band. In other embodiments, the first and second ends of the elastic band are configured to be engaged by a grasping instrument.

Another aspect of the invention is a method of enclosing the heart with any embodiment of the inventive cardiac restraint apparatus. In one embodiment, the invention is a method of at least partially enclosing a heart with a cardiac restraint apparatus that includes a jacket. The method comprises the steps of: a) making a surgical incision to provide an entry point for the cardiac restraint apparatus; b) introducing a cutting tool through the incision and using the cutting tool to make an opening in the pericardium through which the cardiac restraint apparatus can be advanced into engagement with the heart; c) advancing the cardiac restraint apparatus through the incision and the opening into engagement with the heart; and d) sweeping the jacket along the heart to at least partially enclose the heart in the jacket. The surgical incision can be a subxiphoid incision, a transxiphoid incision, a thorascopic incision or another incision.

An alternative embodiment of the inventive method includes the steps of: a) making a surgical incision to provide an entry point for an endoscopic cannula; b) inserting the endoscopic cannula into the surgical incision, wherein the endoscopic cannula has at least one access port; c) advancing the endoscopic cannula to the pericardium under endoscopic visualization; d) introducing a cutting tool into the access port of the endoscopic cannula; e) making an opening in the pericardium using the cutting tool, through which the cardiac restraint apparatus can be advanced into engagement with the heart; f) advancing the endoscopic cannula into the pericardium through the opening; g) advancing the cardiac restraint apparatus into at least one access port of the endoscopic cannula into engagement with the heart; h) sweeping the jacket along the heart to at least partially enclose the heart in the jacket.

Another embodiment of a method according to the invention uses the embodiment of the cardiac restraint apparatus that includes a jacket and one or more guide tubes. In this method, the step of enclosing the heart with the cardiac restraint apparatus includes the steps of: a) advancing a tacking instrument into at least one access port of the endoscopic cannula to access the pericardium; b) tacking the rim of the jacket to the posterior pericardium using the tacking instrument; and c) manipulating the guide tubes of the cardiac restraint instrument to sweep the jacket over the anterior aspect of the heart thereby at least partially enclosing the heart with the jacket. The jacket is then tightened around the heart by reducing the diameter of the opening of the jacket by pulling the end portion of the strand away from the heart while pushing the knot pusher against the slipknot.

Another embodiment of a method according to the invention uses the embodiment of the cardiac restraint apparatus that includes a jacket and one or more handles. In this method, the step of enclosing the heart with the cardiac restraint apparatus includes the steps of: a) advancing one or more guide strands into at least one access port of the endoscopic cannula, the one or more guide strands having a sufficient length to enable the proximal ends of the one or more guide strands to be grasped outside the body when the distal ends of the guide strands are positioned near the heart; b) advancing a tacking instrument into at least one access port of the endoscopic cannula; c) tacking the one or more guide strands to the posterior pericardium using the tacking instrument; d) passing the one or more guide strands through the one or more handles on the rim; and e) using the guide strands to manipulate the jacket, thereby at least partially enclosing the heart with the jacket.

Another embodiment of a method of restraining the heart with a cardiac restraint apparatus involves a cardiac restraint apparatus that includes an elastic band. The method comprises the steps of: a) making a surgical incision to provide an entry point for the cardiac restraint apparatus; b) introducing a cutting tool through the incision and using the cutting tool to make an opening in the pericardium through which the cardiac restraint apparatus can be advanced into engagement with the heart; c) advancing the cardiac restraint apparatus through the incision and the opening into engagement with the heart; and d) restraining the heart with the elastic band by securing the elastic band around the heart. This method includes methods in which the surgical incision is a subxiphoid incision, a trans-xiphoid incision, and a thorascopic incision.

An alternative embodiment of this method includes the steps of: a) making a surgical incision to provide an entry point for an endoscopic cannula; b) inserting the endoscopic cannula into the surgical incision, wherein the endoscopic cannula has at least one access port; c) advancing the endoscopic cannula to the pericardium under endoscopic visualization; d) introducing a cutting tool into the access port of the endoscopic cannula; e) making an opening in the pericardium using the cutting tool, through which the cardiac restraint apparatus can be advanced into engagement with the heart; f) advancing the endoscopic cannula into the pericardium through the opening; g) advancing the cardiac restraint apparatus into at least one access port of the endoscopic cannula into engagement with the heart; and h) restraining the heart with the elastic band by securing the elastic band around the heart.

In the methods using the cardiac restraint apparatus that includes at least one elastic band, in one embodiment the step of restraining the heart with the cardiac restraint apparatus can include the steps of: a) advancing a tacking instrument into the opening in the pericardium (or, in the minimally invasive methods, into the access port of the endoscopic cannula to access the pericardium); b) tacking the elastic band to the posterior pericardium at a point between the first end and the second end; c) grasping the first portion, moving the first portion to the anterior aspect of the heart, and tacking the first portion to the pericardium overlying the anterior aspect of the heart; d) grasping the second portion, moving the second portion over the anterior aspect of the heart, and tacking the second portion to the pericardium overlying the anterior aspect of the heart; and e) attaching (preferably by tacking or clipping) the first and second portions together (preferably at a location overlying the anterior aspect of the heart) to provide a calibrated tension on the heart. The steps of grasping the first and second portions of the elastic band may be performed with any of a variety of grasping tools, for example a clip applier.

DETAILED DESCRIPTION

As defined in this application, the word "distal" is used to describe that portion of the apparatus (or that direction of movement) which extends away from the user during use, and the word "proximal" is used to describe that portion of the apparatus (or that direction of movement) that extends toward the user during use.

Figure 1:
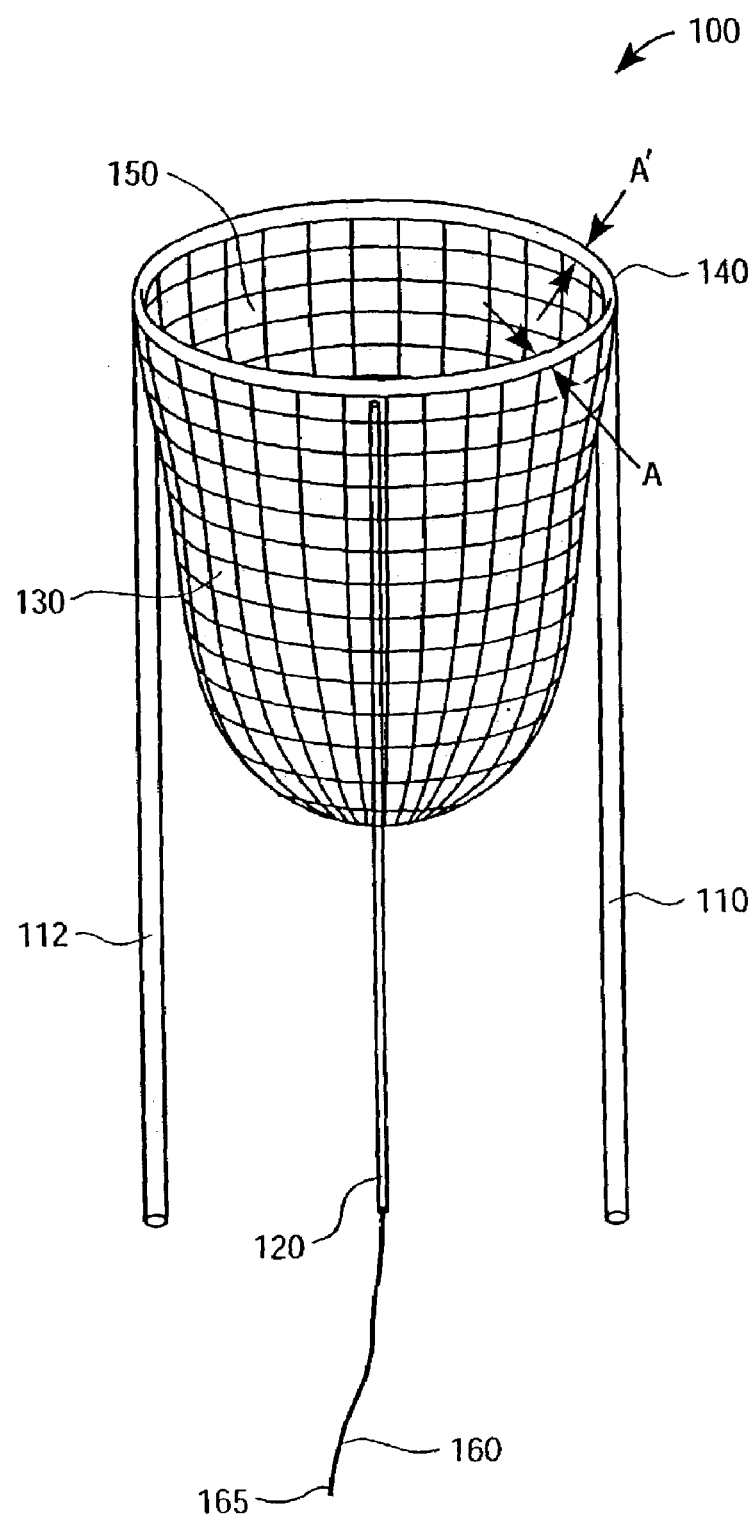
FIG. 1 is a perspective view of one embodiment of a cardiac restraint apparatus of the present invention.

FIG. 1 illustrates a preferred embodiment of a cardiac restraint apparatus 100 which embodies an aspect of the invention. Cardiac restraint apparatus 100 comprises jacket 130 and rim 140, the rim 140 defining opening 150 sufficiently large to receive a heart. Jacket 130 is attached to rim 140 along substantially the entire perimeter of the open end of jacket 140. The apparatus further comprises knot pusher 120 and strand 160 having end 165 which extends through knot pusher 120. The apparatus also includes guide tubes 110 and 112, removably attached to rim 140. Strand 160 extends around rim 140.

Jacket 130 can be constructed of a wide variety of materials, but generally it should be constructed from materials that are biocompatible and non-toxic to bodily tissue, for example distensible or non-distensible mesh fabric constructed from silicon rubber, nylon, polyurethane, polyester, polytetrafluoroethylene (PTFE), expanded PTFE (ePTFE), polypropylene, stainless steel, and impregnated elastomers such as nylon in polyurethane or nylon in silicon rubber. While FIG. 1 illustrates jacket 130 as being open at one end and closed at the other, the invention also contemplates a jacket that is open at both ends.

Rim 140 is preferably hollow, for example constructed as a hollow tube or a folded fabric sleeve, which is capable of receiving and containing strand 160. Rim 140 may be constructed separately from any biocompatible, flexible material (such as biocompatible fabrics and plastics) and attached to jacket 130 around the perimeter of opening 150, or may alternatively be constructed by simply folding and securing the mesh fabric of jacket 140 around opening 150 to create a hollow fabric sleeve.

Knot pusher 120 can be constructed from any suitable material capable of being formed into a hollow tube, for example rigid and flexible plastics, metals such as stainless steel, and wood.

Strand 160 can be constructed from any conventional surgical suture material, for example nylon, silk, steel, catgut, and conventional bioabsorbable suture materials such as polymers and copolymers of lactide, glycotide, para-dioxanone and trimethylene carbonate. At least one end 165 of strand 160 is disposed within knot pusher 120. As used in the present invention, the term "strand" is deemed to include any of a variety of strings, fibers, wires, or sutures capable of being tied into a slipknot.

Figure 2:
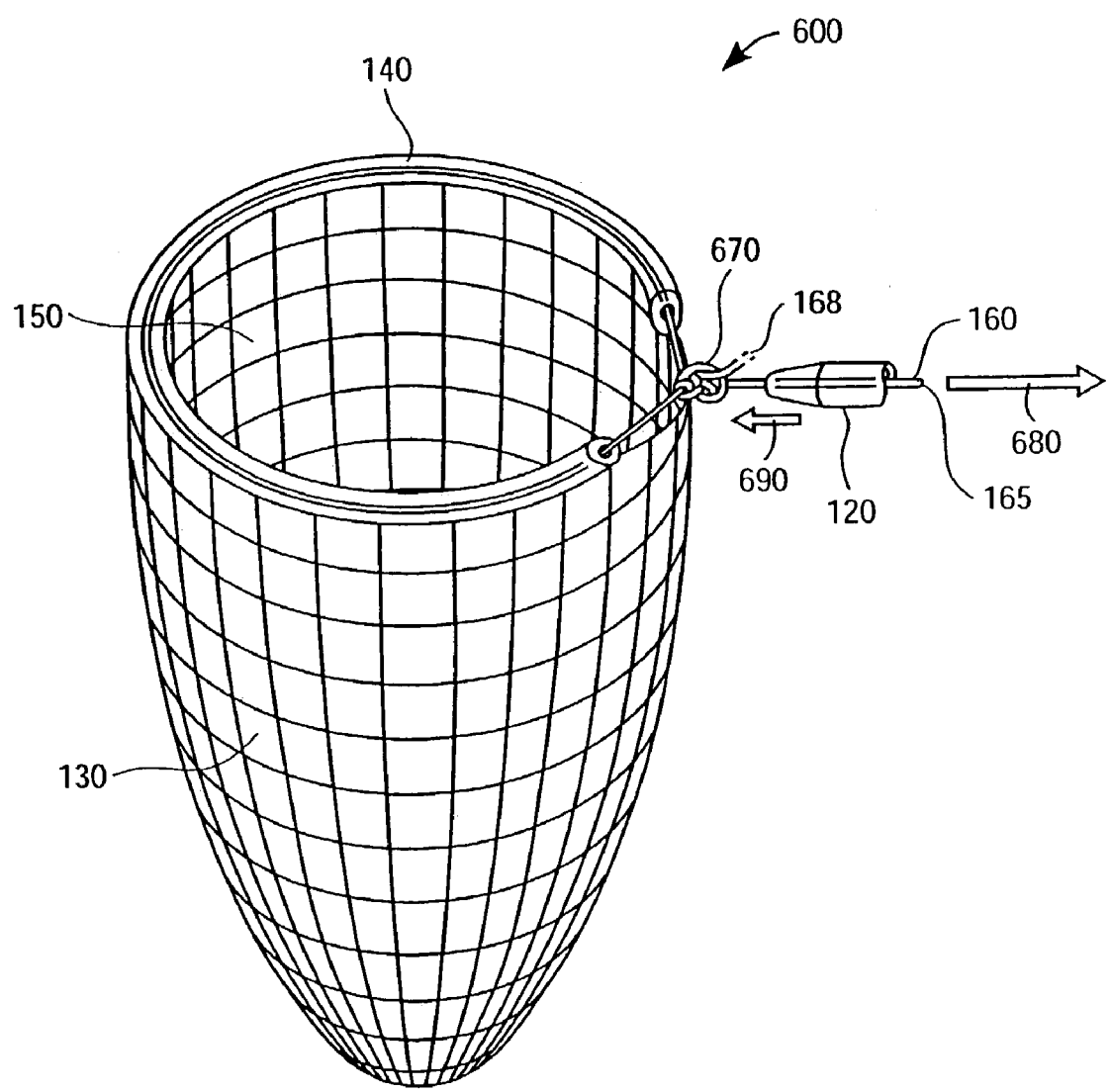
FIG. 2 is a partial cross sectional view of the operation of the knot pusher in reducing the diameter of the opening of an embodiment of a cardiac restraint apparatus according to the present invention.

FIG. 2 best illustrates the structural relationship between knot pusher 120, rim 140 and strand 160. In this figure, guide tubes 110 and 112 have been omitted for clarity. At the juncture where knot pusher 120 meets rim 140, strand 160 is tied into slipknot 670. At least one end 165 of strand 160 is disposed within knot pusher 120, which in this figure is illustrated as being tapered. Such taper is entirely optional and in no way limits the invention. The operation of knot pusher 120 is illustrated using arrows 680 and 690 in FIG. 2. Strand 160 is pulled away from the heart in the direction of arrow 680 (proximally) while knot pusher 120 is pushed against the slipknot in the direction of arrow 690 (distally). The distal movement of knot pusher 120 pushes knot pusher 120 against slipknot 670, holding slipknot 670 while pulling strand 160 away from the heart and causing a reduction of the diameter of opening 150, thereby tightening jacket 130 around the heart (not shown).

Figure 3:
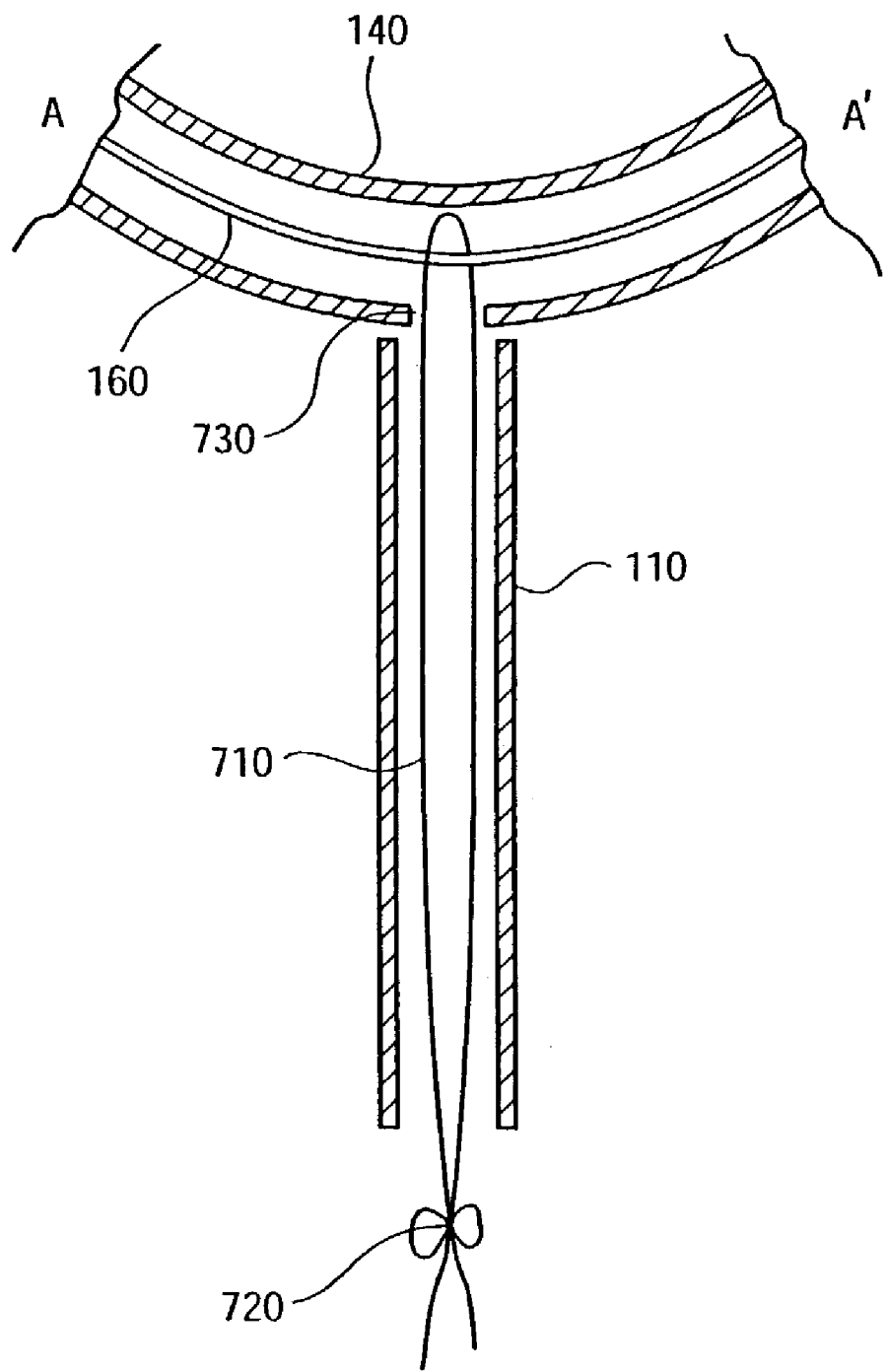
FIG. 3 is a cross sectional view of a portion of the rim of a jacket of an embodiment of a cardiac restraint apparatus according to the present invention.

Referring again to FIG. 1, the illustrated embodiment of a cardiac restraint apparatus according to the invention also includes one or more guide tubes 110 and 112, removably attached to rim 140. Guide tubes 110 and 112 may be attached by any suitable detachable means, for example by having perforations at the site of attachment. A preferable means of removably attaching guide tubes 110 and 112 to rim 140 will be described with reference to FIG. 3. FIG. 3 is a cross sectional view of a portion of the rim of a jacket of a cardiac restraint apparatus according to the invention, more specifically, section AA' of rim 140 as illustrated in FIG. 1. In this embodiment, rim 140 includes an opening 730 at the site where guide tube 110 meets rim 140. Connecting strand 710 extends within guide tube 110, is looped over strand 160 (strand 160 extends within and around rim 140), and is tied into knot 720. Guide tube 110 is removable by cutting connecting strand 710 or unraveling knot 720 and disengaging connecting strand 720 from strand 160, thereby disengaging guide tube 110 from rim 140. Guide tubes 110 and 112 can be constructed from any suitable material capable of being formed into a hollow tube, for example rigid and flexible plastics, metals such as stainless steel, and wood. Preferably guide tubes 110 and 112 have a diameter of about 1 mm to 1.5 mm.

Figure 4:
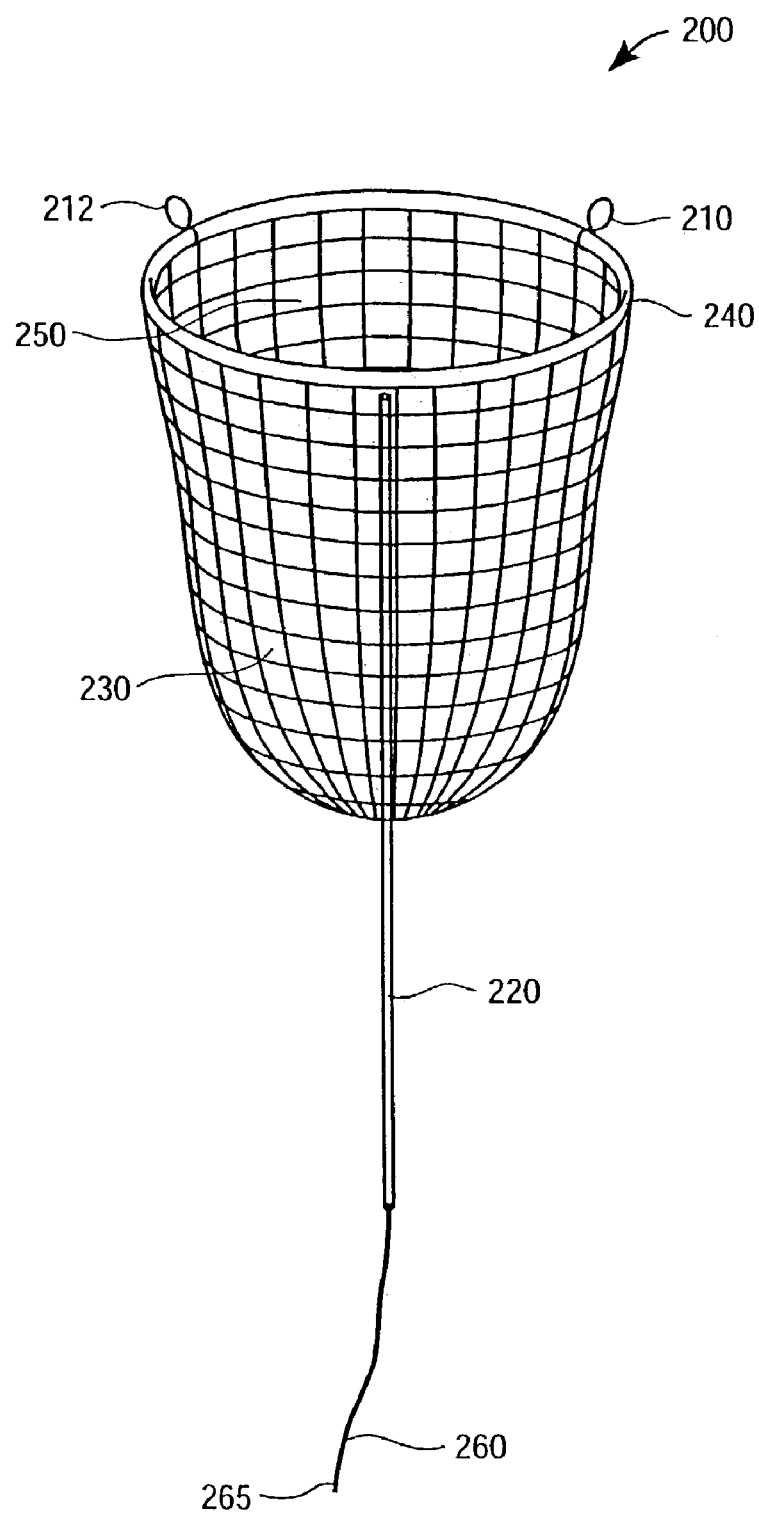
FIG. 4 is a perspective view of an alternative embodiment of a cardiac restraint apparatus of the present invention.

An alternative embodiment of a cardiac restraint apparatus according to the present invention is illustrated in FIG. 4. Cardiac restraint apparatus 200 is similar to the cardiac restraint apparatus 100 of FIG. 1, except that rather than including guide tubes, it includes at least one handle for guiding the apparatus during performance of a surgical procedure. Thus, the guide tubes 110 and 112 shown in FIG. 1 and the handles 210 and 212 shown in FIG. 2 are alternative embodiments of guide elements to help in guiding the placement of the cardiac restraint apparatus around the heart during surgery. Specifically, this alternative embodiment of a cardiac restraint apparatus according to the invention comprises jacket 230 and rim 240, the rim 240 defining opening 250 sufficiently large to receive a heart. Jacket 230 is attached to rim 240 along substantially the entire perimeter of the open end of jacket 240. The apparatus further comprises knot pusher 220 and strand 260 having end 265 which extends through knot pusher 220 and extends around rim 240. The apparatus also includes handles 210 and 212 attached to rim 240.

Handles 210 and 212 may be constructed from any conventional surgical suture material, for example nylon, silk, steel, catgut, and conventional bioabsorbable suture materials such as polymers and copolymers of lactide, glycotide, para-dioxanone and trimethylene carbonate. Handles 210 and 212 may be attached to rim 240 by any suitable means, for example using adhesives, welding, or tying handles 210 and 212 around rim 240. Optionally, handles 210 and 212 may be removably attached to rim 240, for example by using a perforated strap (not shown).

Figure 5:
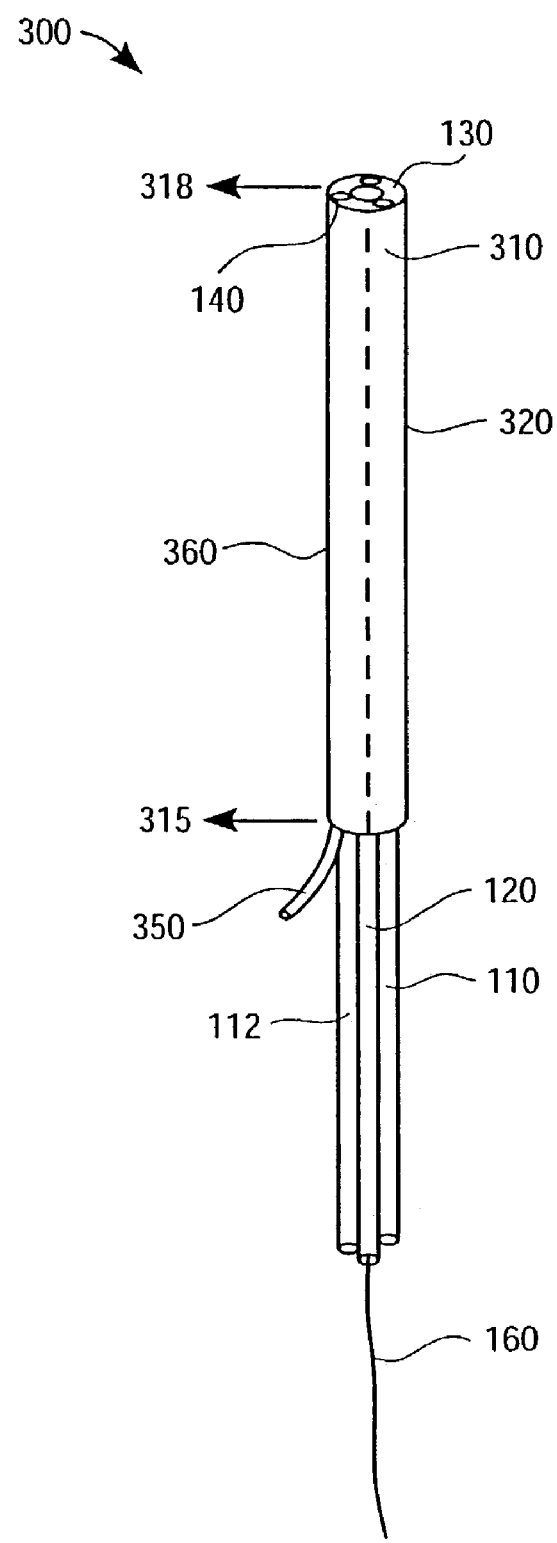
FIG. 5 is a perspective view of a sheathed cardiac restraint apparatus of the present invention.

FIG. 5 is a perspective view of a sheathed embodiment of the cardiac restraint apparatus of the present invention. Sheathed apparatus 300 is the cardiac restraint apparatus illustrated in FIG. 1 that has been placed in a compact state and sheathed within sheath 320. Jacket 130 and rim 140 of apparatus 100 are folded, creased or crumpled to reduce their profile before being enclosed by sheath 320. Jacket 130 moves into a non-compact state, illustrated in FIG. 1, when sheath 320 is removed.

Sheath 320 can be constructed from any flexible material, including but not limited to polyethylene, polyvinylchloride, and teflon. Sheath 320 may be of any structure suitable to enclose jacket 130. Preferably, sheath 320 includes a generally cylindrical body 360 having a proximal end 315 and a distal end 318, sheath body 360 defining perforations 310 along sheath body 360, and pull tab 350 attached to proximal end 315. Preferably, perforations 310 are longitudinally positioned. Sheath body 360 defines a lumen having an inner diameter of preferably 7 mm to 10 mm. Sheath 320 is removable from apparatus 300 by tearing sheath body 360 along perforations 310. This removal is more easily accomplished by implanting sheath 320 with a pull tab 350 extending out from the proximal end 315 of sheath body 360. Pulling of pull tab 350 away from the apparatus 300 results in tearing of sheath body 360 along perforations 310 and removal of the torn sheath 320 from jacket 130.

Figure 9A:
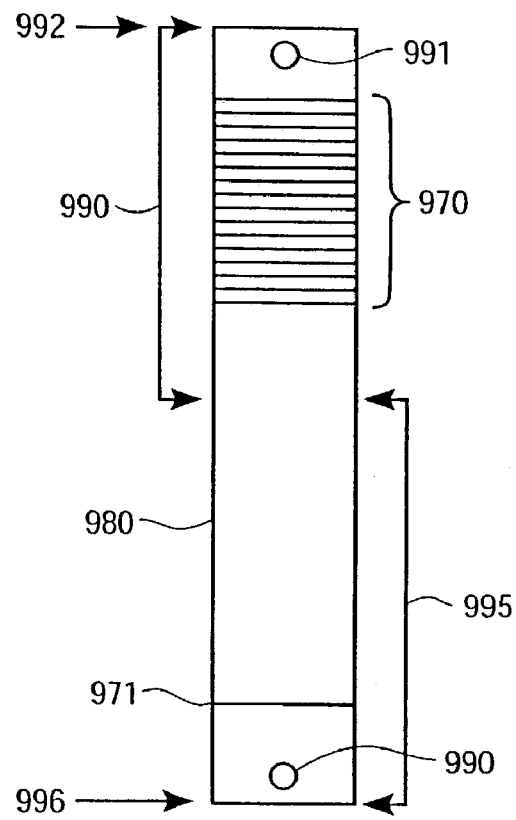
FIGS. 9A through 9B are perspective views of an alternative embodiment of a cardiac restraint apparatus according to the present invention.
Figure 9B:
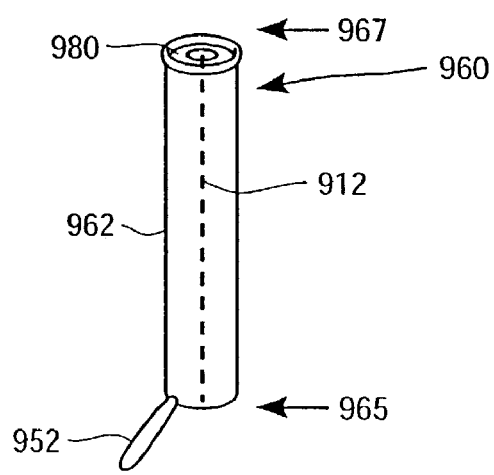

Another alternative embodiment of a cardiac restraint apparatus according to the present invention is illustrated in FIGS. 9A–9B. In this embodiment, cardiac restraint apparatus 960 comprises at least one elastic band 980 having a first portion 990 terminating at a first end 992 and a second portion 995 terminating at a second end 996, with the first portion 990 and the second portion 995 of the elastic band 980 being joined together at a location between first end 992 and second end 996. Thus, elastic band 980 may be constructed of two separate portions that have been attached together, or alternatively, it may be one continuous piece. Elastic band 980 is constructed from any flexible material, including but not limited to silicon rubber, nylon, polyurethane, polyester, polytetrafluoroethylene (PTFE), expanded PTFE (ePTFE), polypropylene, and impregnated elastomers such as nylon in polyurethane or nylon in silicon rubber. Preferably, elastic band 980 has a width of about 1 cm, and a thickness of approximately 1–3 mm.

Each elastic band can be sheathed with a sheath, such as sheath 962 of FIG. 9B, when introduced into the patient. Sheath 962 has a generally cylindrical body having a proximal end 965 and a distal end 967, and can be constructed from any flexible material, including but not limited to polyethylene, polyvinylchloride, and teflon. Sheath 962 can be of any structure suitable to enclose elastic band 980 or two or more of elastic bands 980, preferably enclosing elastic band 980 in a rolled configuration as illustrated in FIG. 9B. Sheath 962 can define perforations 912, such that the sheath can be removed by tearing along perforations 912. Preferably, perforations 912 are longitudinally positioned. The sheath can also include a pull tab 952 that is attached to the proximal end 965 of sheath 962, for pulling the sheath away from the apparatus. Elastic band 980 may also include calibrated markings 970 for calibrating the tension of the elastic band 980. In use, a surgeon can calibrate the tension of elastic band 980 using calibrated markings 970 and markinh 971 by stretching elastic band 980 from its relaxed state and noting the number of calibrated markings 970 overlapped by marking 971.

Optionally, the first and second ends of the elastic band 980 are configured to be engaged by a grasping instrument, for example by including openings 990 and 991 suitably sized to receive a grasping instrument.

Another aspect of the present invention is a class of methods of restraining the heart using any embodiment of the inventive cardiac restraint apparatus. While any suitable surgical approach to the heart may be used, for example trans-xiphoid or thoroscopic incisions, the preferred incision is a subxiphoid incision large enough to allow for insertion of a cannula for performing minimally invasive surgery, preferably about 2 cm. An apparatus having a cannula through which the cardiac restraint apparatus of the present invention can be deployed, and methods of using the apparatus, are disclosed in detail in co-pending application Ser. No. 09/635,345, hereby incorporated by reference in its entirety.

Briefly, the surgical apparatus preferably used to deploy the cardiac restraint apparatus through a subxiphoid incision is an endoscopic cannula comprising a cannula, a transparent tip located at the distal end of the cannula, and an endoscope preferably positioned at the distal end of the cannula. The cannula has at least one lumen, and one or more additional lumens for advancement of surgical tools. The transparent tip is preferably tapered to provide better visualization by offsetting and retracting tissue away from the field of view. Still more preferably, the transparent tip has a generally conical shape. The transparent tip is preferably removable and replaceable, such that it may be removed when it is desired to obtain a sharper image of the surgical site.

In a preferred embodiment, the endoscopic cannula may comprise one or more access ports positioned at a proximal end of the cannula, for receiving surgical instruments into an instrument lumen of the cannula. Such a preferred endoscopic cannula further comprises an endoscopic eyepiece, skewed relative to the proximal end of the endoscope, for facilitating the viewing of a surgical site through the endoscope while minimizing interference with surgical instruments introduced into the cannula.

Using the methods of this invention, the endoscopic cannula is either directly advanced to the mediastinum or alternatively, a cavity is first dilated and the endoscopic cannula is advanced through the dilated cavity. Once the endoscopic cannula is advanced into the mediastinum, surgical tools are advanced through the one or more access ports, and surgical procedures are performed within the mediastinum. Surgical tools that are used with the endoscopic cannula in the methods of the present invention include a cutting tool for creating an opening in the pericardium, as well as the cardiac restraint apparatus of the present invention.

In directly advancing the endoscopic cannula, the endoscopic cannula is inserted directly into the initial subxiphoid incision and is guided, under endoscopic visualization, to the surgical site. Alternatively, a cavity toward the surgical site may be first dilated using a dilation tool according to this invention, and the cannula may be subsequently advanced within the dilated cavity. The second method is advantageous because as the dilation tool generally has a smaller diameter than the endoscopic cannula, initially inserting the dilation tool minimizes trauma to the heart and reduces the chance of ventricular fibrillation due to irritation of the heart with a large diameter instrument.

The dilation tool optionally used to dilate a cavity for the endoscopic cannula has an inner cannula having an elongated body, a transparent tip at the distal end of the elongated body, an endoscope, and an outer expandable sheath. Preferably, the dilation tool has a small maximal dimension which minimizes trauma to the pericardium upon reaching the pericardium. The inner cannula has a tip having an enlarged region positioned distal to a distal end of the outer expandable sheath. The inner cannula is withdrawn through the outer expandable sheath, and the expandable sheath dilates a cavity concurrent to the retraction of the tip. The expandable sheath exerts a radial force against the surrounding tissue as the tip is retracted through the sheath. The radial force provides a less traumatic dilation than conventional dilation techniques such as using a bougie dilation, in which shear force is directly applied to surrounding tissue.

Once the cavity is dilated, the endoscopic cannula is then inserted into the incision and advanced into the proximal end of the expandable sheath. As the endoscopic cannula is advanced to the pericardium through the sheath, it will also cause the expandable sheath to expand further and dilate the working tunnel to a sufficient size to accommodate the endoscopic cannula. The expandable sheath provides the additional benefit of guiding the endoscopic cannula to the proper position at the pericardium. Alternatively, the endoscopic cannula is inserted directly into the initial incision without dilation.

In order to restrain the heart with a cardiac restraint apparatus of the present invention using the subxiphoid method, the endoscopic cannula is advanced under endoscopic visualization, as described previously, either directly into the initial subxiphoid incision or after first dilating a cavity using a dilation tool as described herein. Upon reaching the pericardium, a flap of the pericardium is gripped using a pericardial entry instrument as described herein, and the flap is cut using a cutting tool to create an opening in the pericardium. In cutting the pericardium, this invention contemplates cutting the flap of the pericardium away from the underlying heart.

The subxiphoid approach method is particularly advantageous as it enables the surgeon to access all regions of the heart, that is a 360 degree access capability including the anterior, posterior, left and right regions of the heart. Using one embodiment of this method, the cannula is initially inserted into the pericardium via an incision near the apex of the heart and then swept over the anterior and posterior surfaces of the heart. It should be noted that while entry near the apex of the heart aids the surgeon by providing a landmark for easier recognition of the position of the endoscopic cannula within the body, such an entry is not required by this invention and other entry positions, such as entry in the posterior region of the heart, are also contemplated. Once inside the pericardium, the cannula can be maneuvered around the heart substantially because of the subxiphoid entry and the flexibility of soft tissue around the heart. Thus, all regions of the heart may be accessed without the need for invasively lifting or rotating the heart to access posterior or lateral vessels and structures.

The subxiphoid access method is advantageous over conventional methods. As this procedure is performed under endoscopic visualization it is minimally invasive. In addition, as the approach is through a subxiphoid incision, there is no need to go through the pleural cavity and thus no need to deflate the lungs. Also, although the method requires only a single incision (that is, the subxiphoid incision), using this method access is gained to all regions of the heart. Conventionally, such extensive access to the heart has only been possible using invasive methods such as pericardial window, open heart surgery, or port access surgery using several incisions and ports. Thus, using the subxiphoid access method as herein described, the surgeon may access all regions of the heart with a single incision, without needing to go through the pleural cavity.

The endoscopic cannula with the transparent tapered tip is used to bluntly dissect a path to the pericardium, through the fat and connective tissue. Direct visualization allows verification that the pericardial surface is clean and devoid of adherent fat. Application of the pericardial entry instrument may occur under visual guidance on an exposed pericardial surface.

Figure 6A:
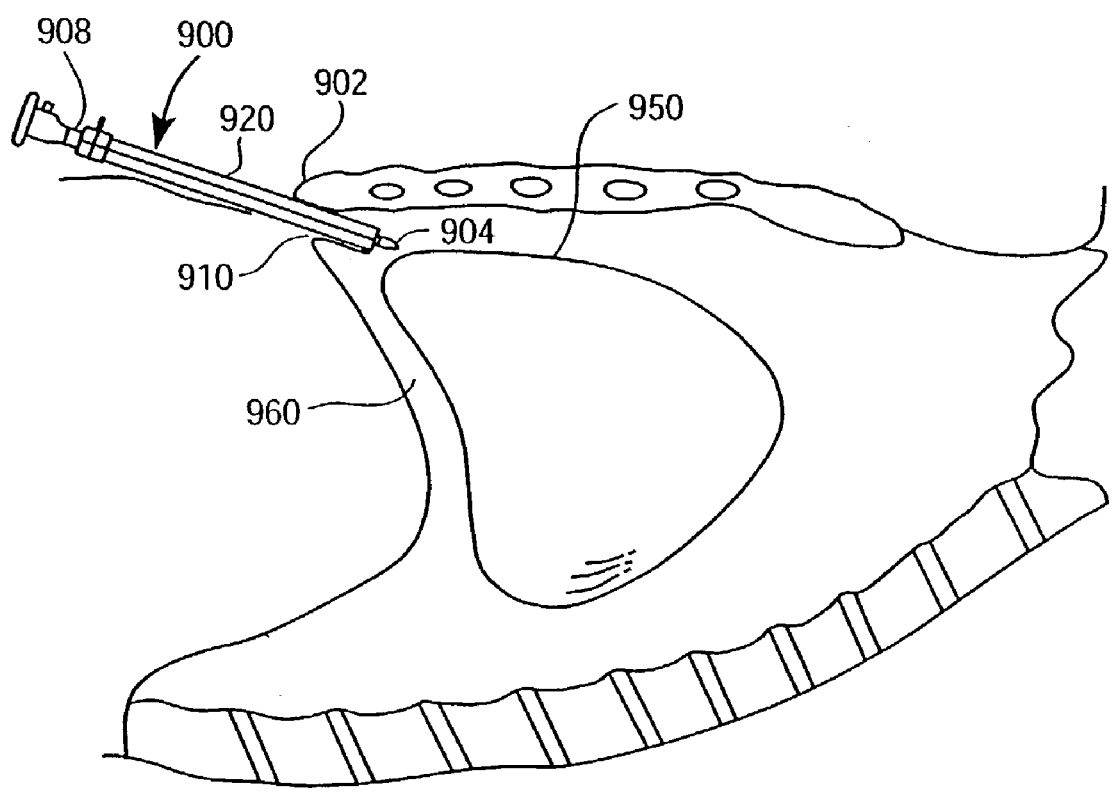
FIGS. 6A through 6G are partial cross sectional views of a method of accessing the heart with an endoscopic cannula using a subxiphoid approach.

The subxiphoid method for accessing the heart is illustrated in more detail in FIGS. 6A–6G. First, a subxiphoid incision is made overlying an entry point for a surgical procedure. The subxiphoid incision is preferably small, about 2 cm. The subcutaneous tissue below the incision is bluntly dissected to expose the linea alba, which is also incised. Referring now to FIG. 6A, dilation tool 900, comprising an inner cannula 908 having tapered tip 904 and an outer expandable sheath 920, is inserted into the subxiphoid incision 910. Tapered tip 904 of inner cannula 908 bluntly dissects a cavity responsive to the advancement of the dilation tool 900. Dilation tool 900 is then positioned on the posterior aspect of the xiphoid process 902. Dilation tool 900 is then advanced within the mediastinum 960 under endoscopic visualization (tapered tip 904 is transparent to allow endoscopic visualization). A laparoscopic endoscope with an attached CCD chip camera (not shown) can be used to accomplish endoscopic visualization. Since the pericardium 950 is a thin membrane, visualization of the beating heart through the endoscope underneath a translucent membrane indicates correct positioning of the dilation tool 900 on the anterior surface of the pericardium 950.

Figure 6B:
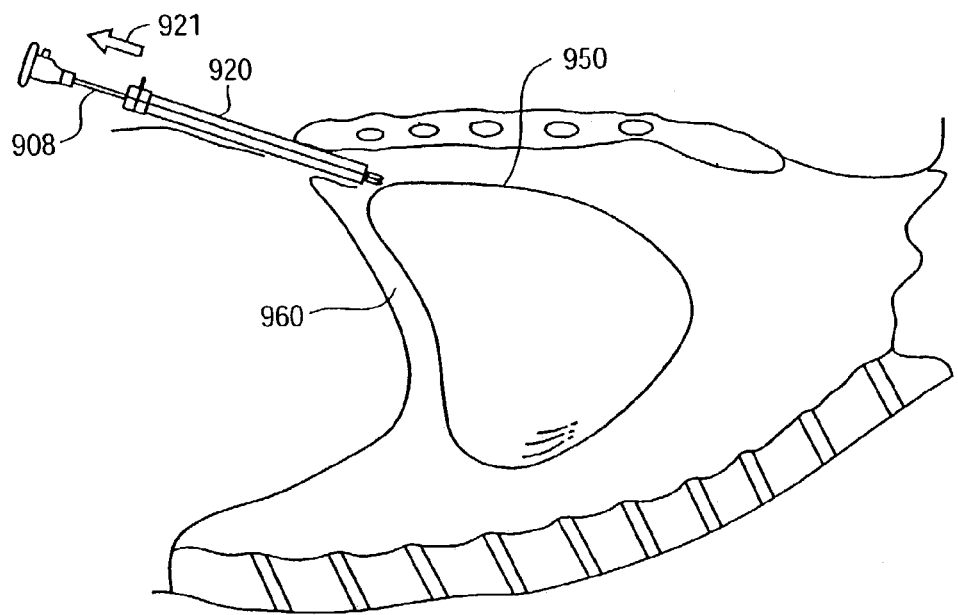

In FIG. 6B, Following advancement of the dilation tool 900 to the desired position in the body, expandable sheath 920 is held in place as inner cannula 908 is retracted through expandable sheath 920 in the direction indicated by arrow 921. Inner cannula 908 has an enlarged region near its tip (not shown) which causes expansion of the sheath 920 during retraction of inner cannula 908. This expansion of sheath 920 dilates the tissue adjacent to the length of expandable sheath 920 to at least the maximal dimension of the enlarged region.

With expandable sheath 920 in place, large diameter instruments can be sequentially inserted through the proximal end of expandable sheath 920 without exerting shear force on the tissue cavity. Expandable sheath 920 accommodates instruments of varying diameters and cross-sections. Thus, leaving expandable sheath 920 in place maintains a dilated cavity to the desired surgical site, facilitating the advancement of the next instrument to be used in the procedure to the correct position within the body.

Figure 6C:
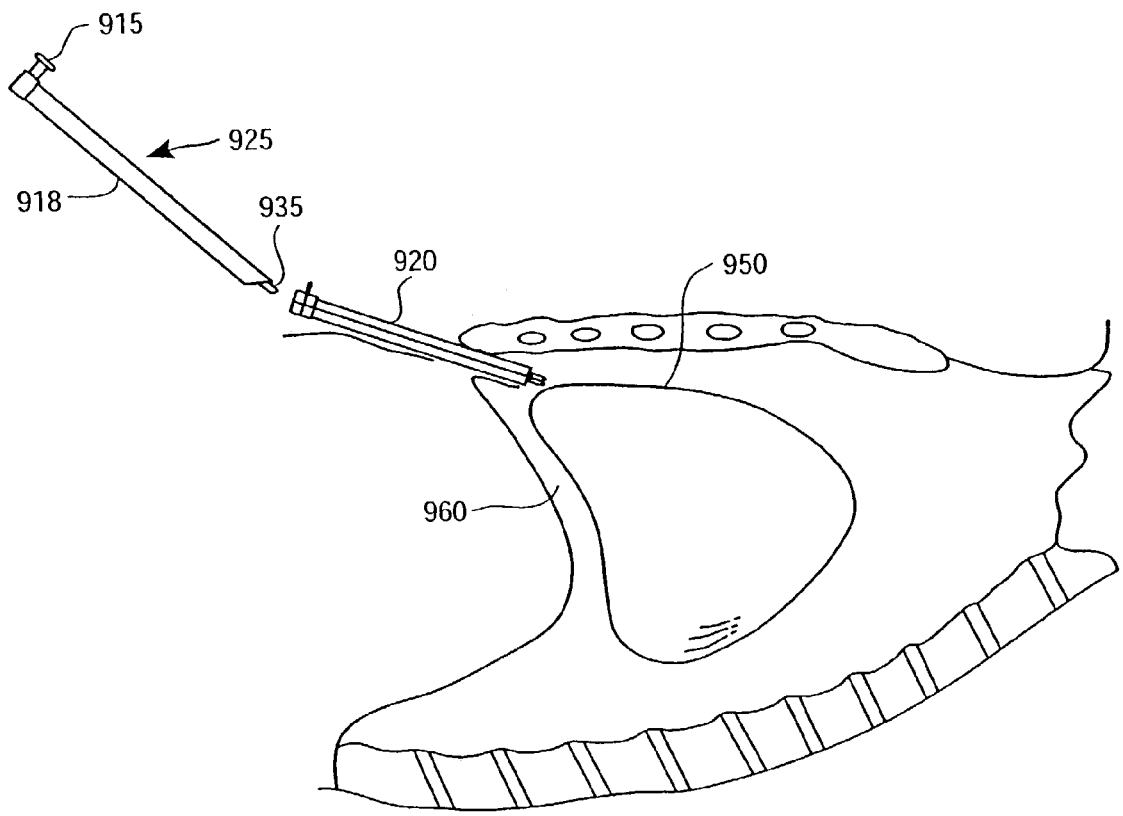
Figure 6D:
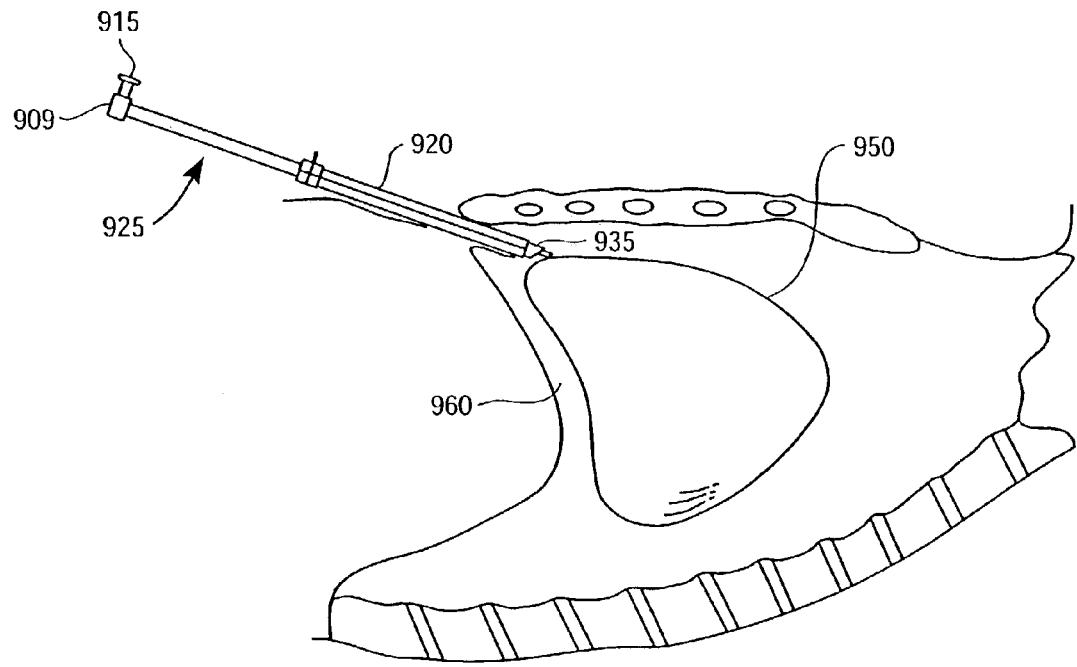

FIG. 6C illustrates the step of introducing an endoscopic cannula 925 with transparent tapered tip 935, used in the methods of the present invention. Endoscopic cannula 925 is about to be inserted into expandable sheath 920, which is expanded to accommodate the larger diameter of the endoscopic cannula 925. Endoscopic cannula 925 has an elongated body 918 which defines one or more lumens. One of the lumens may be used as an endoscopic lumen to house an endoscope, while the other lumen may be used as an access port 909 for housing surgical apparatus, advanced either concurrently or sequentially, as will be discussed more specifically below. In order for the endoscopic cannula to be used for introducing a cardiac restraint apparatus according to the present invention, the access port 909 should be approximately 12–15 mm in diameter. FIG. 6D shows endoscopic cannula 925 in position inside expandable sheath 920, with tapered tip 935 adjacent to pericardium 950.

Figure 6E:
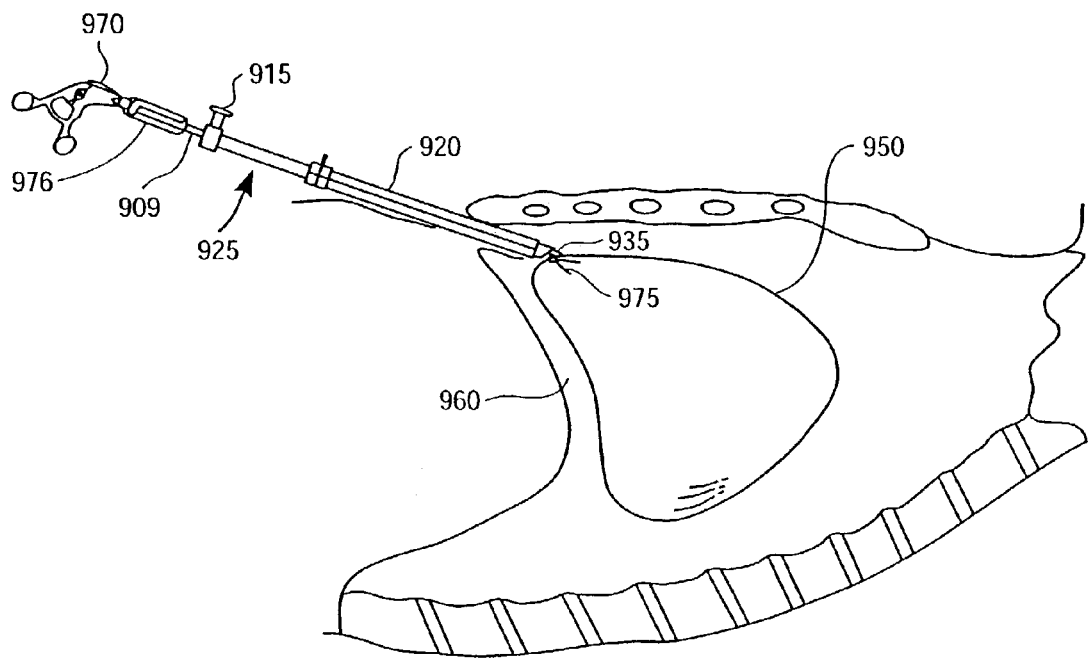

Referring now to FIG. 6E, cutting tool 970 (including grasping jaws 975 and rotatable cutting tube 976) is inserted into access port 909 of endoscopic cannula 925 to cut an opening in the pericardium 950 to access the heart. Cutting tool 970 is manipulated to grasp the pericardium 950 with the grasping jaws 975, followed by rotation and distal translation of the cutting tube 976, cutting an opening in the pericardium 950 to permit insertion of endoscopic cannula 925 into the pericardium 950.

Figure 6F:
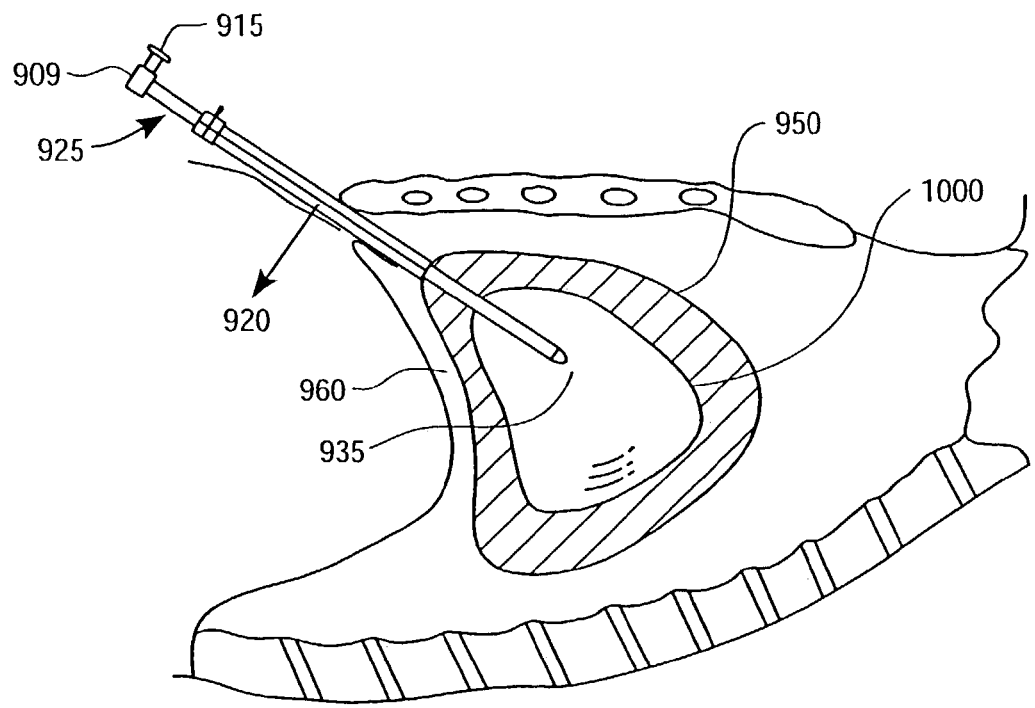
Figure 6G:
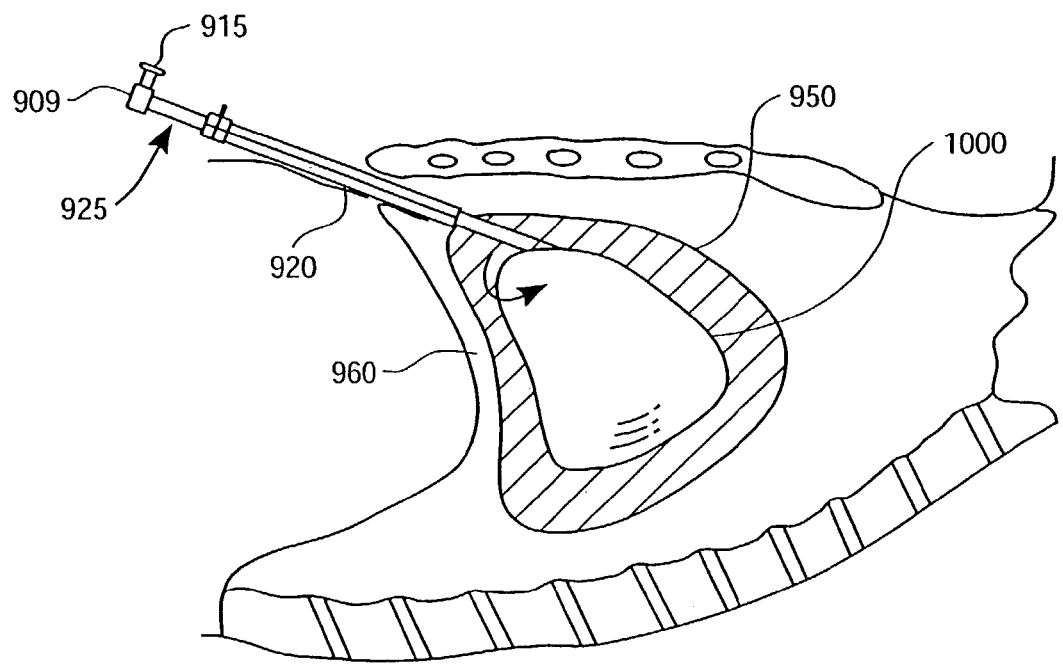

FIGS. 6F and 6G illustrate the maneuverability of endoscopic cannula 925 once it is inserted into the pericardium through the opening created by cutting tool 970. Once inside the pericardium, endoscopic cannula 925 can be swept around the heart 1000 over the anterior and posterior surfaces of the heart 1000 (e.g. from the position shown in FIG. 6F to that shown in FIG. 6G). As shown in FIGS. 6F and 6G, endoscopic cannula 925 is maneuvered around the heart 1000 in such a way that all regions of the heart may be accessed. The endoscopic cannula can be maneuvered because of the subxiphoid entry position and the flexibility of soft tissue around the heart, the softness of the tissue allowing the endoscopic cannula to push apart tissue and move around the heart. Thus, all regions of the heart may be accessed without the need for invasively lifting or rotating the heart to access posterior or lateral vessels and structures.

It should be noted that while the above method of accessing the pericardium was described with reference to usage of a dilation tool having an expandable sheath, a dilation tool without an expandable sheath may also be used. In that embodiment, the inner cannula of the dilation tool can be used by itself to dilate a cavity to access the pericardium, and the endoscopic cannula can be inserted into the dilated cavity.

Figure 7A:
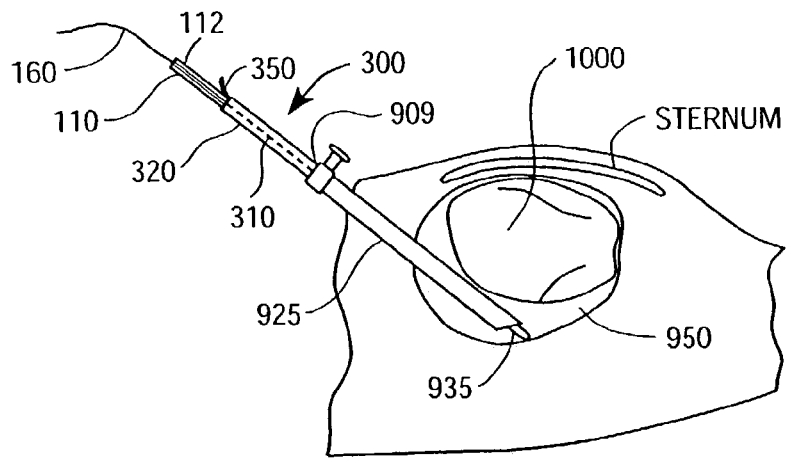
FIGS. 7A through 7D are partial cross sectional views of the operation of an endoscopic cannula and the use of a cardiac restraint apparatus in accordance with the present invention.
Figure 7B:
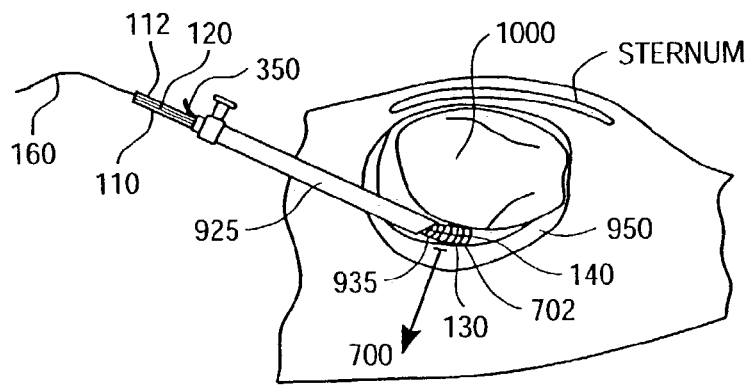

Once the heart is accessed, a cardiac restraint apparatus according to the invention may be introduced and positioned around the heart. FIGS. 7A through 7D demonstrate a method of placement of a cardiac restraint apparatus via subxiphoid incision. While a subxiphoid approach is the preferred method, the methods of this invention are not limited to the subxiphoid approach and other incisions, for example trans-xiphoid and thorascopic, may also be used, with or without the usage of an endoscopic cannula. FIG. 7A illustrates an endoscopic cannula 925 in position on the posterior aspect of the heart 1000 via a subxiphoid approach as previously described, and a sheathed cardiac restraint apparatus 300 according to the invention being inserted into access port 909. Endoscopic cannula 925 also has a second access port, into which a tacking instrument (not shown) is inserted. Alternatively, the tacking instrument is inserted through the lumens defined by each one of guide tubes 110 and 112 in turn instead of through a second access port of endoscopic cannula 925. In this alternative embodiment, guide tubes 110 and 112 each define a lumen sufficiently wide to receive the tacking instrument 700. Guide tubes 110 and 112 are sufficiently long to remain outside of the body while the jacket is placed around the heart.

Next, sheath 320 is removed by pulling pull tab 350 away from the heart, tearing sheath 320 at perforations 310. The removal of sheath 320 frees jacket 130, causing it to unwind from its folded state. The tacking instrument 700 is then used to tack or staple rim 140 to the posterior pericardium near the base of the heart, using guide tubes 110 and 112 to better guide the placement of rim 140 and to hold rim 140 in place in the desired position during tacking. Following placement of tack 702, each guide tube 110 and 112 is detached from rim 140, for example by cutting strand 710 or unraveling knot 720 as illustrated in FIG. 3.

Figure 7C:
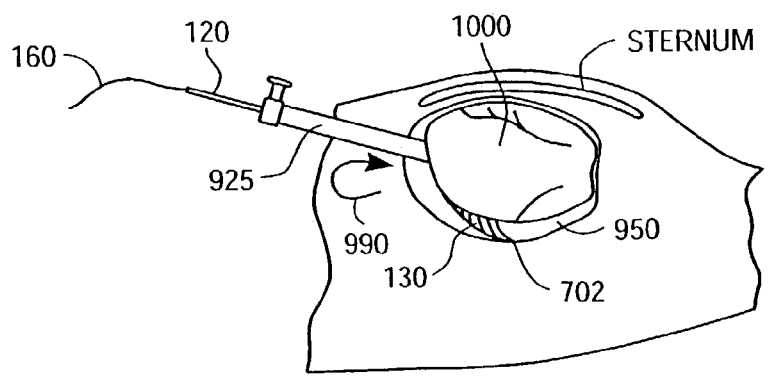
Figure 7D:
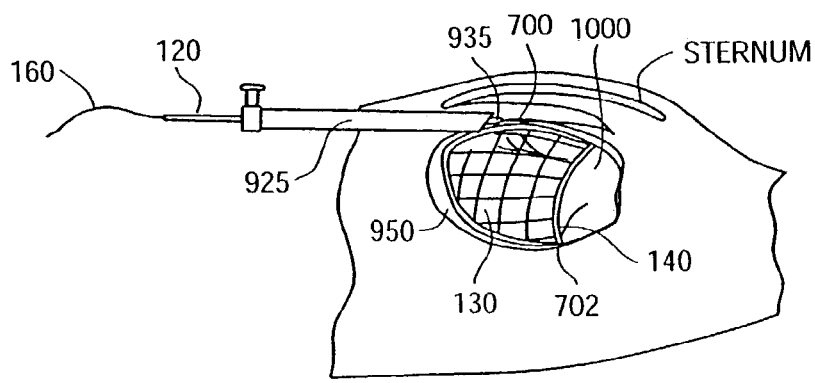

As shown in FIGS. 7C and 7D, endoscopic cannula 925 is then pulled up and over the apex of the heart in the direction of arrow 990, pulling jacket 130 onto the anterior surface of the heart to at least partially enclose the heart with jacket 130. Manipulation of jacket 130 may be aided by enlarging the pericardial opening using a cutting tool as previously described. As shown more clearly in FIG. 2, strand 160 is then pulled away from the heart while knot pusher 120 is pushed against slipknot 670 on rim 140, to tighten jacket 130 around the heart as more clearly illustrated in FIG. 2. Knot pusher 120 is then disengaged from strand 160, and a pair of endoscopic scissors (not shown) are advanced through the cannula to transect the excess tail of strand 160 to conclude the procedure.

Figure 8A:
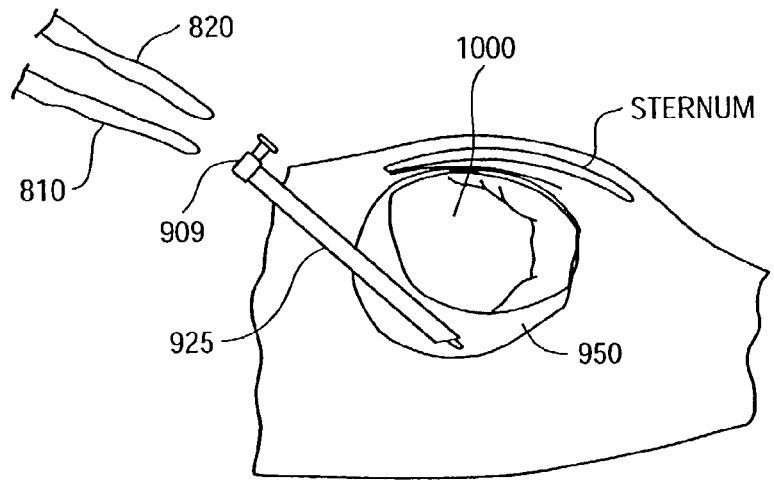
FIGS. 8A through 8C are partial cross sectional views of an alternative method of the operation of an endoscopic cannula and the use of an alternative embodiment of a cardiac restraint apparatus in accordance with the present invention.
Figure 8B:
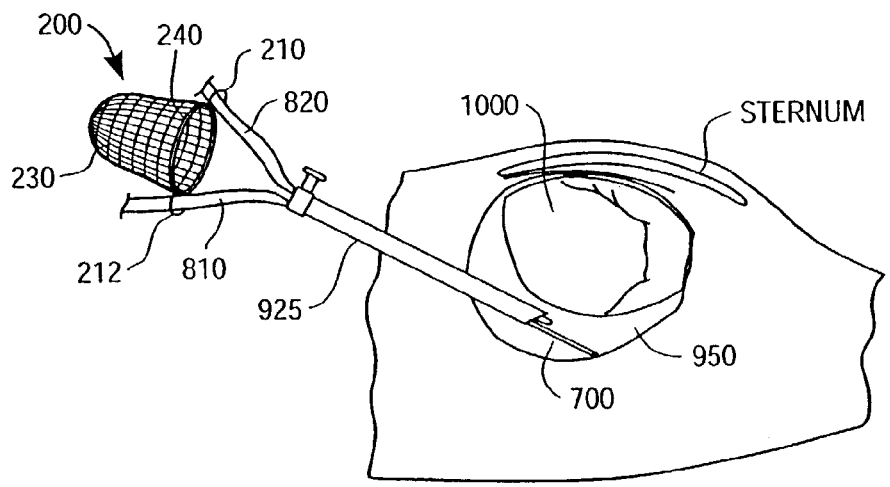
Figure 8C:
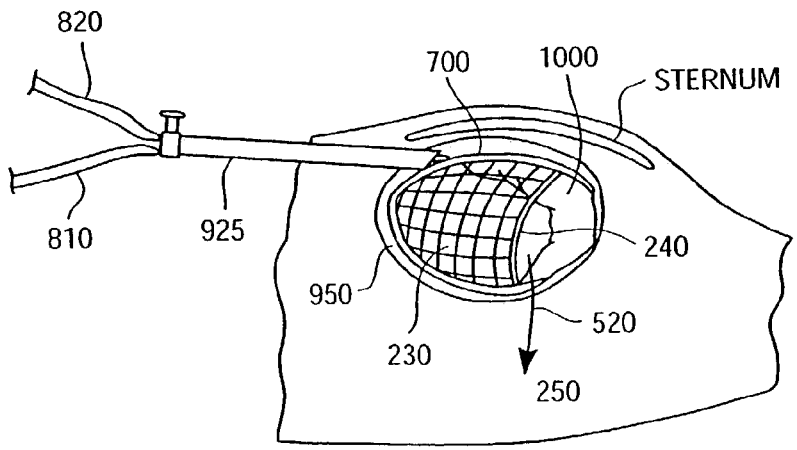

Alternatively, the endoscopic cannula may be advanced to the posterior pericardial space without deployment of the cardiac restraint apparatus, as shown in FIGS. 8A–8C. This alternative method uses an alternative embodiment of a cardiac restraint apparatus, as shown in FIG. 4 and described above in detail. Referring now to FIG. 8A, endoscopic cannula 925 has been positioned within the pericardium as described above. Guide strands 810 and 820 are then introduced into endoscopic cannula 925 via access port 909. Guide strands 810 and 820 can be constructed from any conventional surgical suture material, for example nylon, silk, steel, catgut, and conventional bioabsorbable suture materials such as polymers and copolymers of lactide, glycotide, para-dioxanone and trimethylene carbonate.

Next, tacking instrument 700 is introduced into access port 909 (or alternatively, into a second access port, not shown) as illustrated in FIG. 8B. Guide strands 810 and 820 are tacked to the posterior pericardium using tacking instrument 700. Alternatively, guide strands 810 and 820 can be tied to a tack in the tacking instrument 700 prior to its introduction through access port 909. Guide strands 810 and 820 are then looped through the handles 210 and 212 attached to rim 240 of cardiac restraint apparatus 200, as shown in FIG. 8B. While in this embodiment of the method jacket 230 is in its unsheathed state, jacket 230 may alternatively be sheathed as previously described. Cardiac restraint apparatus 200 is pushed, guided by guide strands 810 and 820, into position posterior to the heart. Guide strands 810 and 820 may be tied extracorporeally, and the knots pushed up to the previously placed tacks, to secure the posterior portion of jacket 230. At this point, if the sheathed configuration of jacket 230 is used, the jacket is unsheathed as previously described, and opening 250 of the jacket 230 is pulled inferiorly around the apex of the heart, then advanced anteriorly into position at the base of the heart as shown in FIG. 8C. The knot pusher at the anterior mouth of the jacket is cinched down at the base of the heart as shown in more detail in FIG. 2 and as previously described, to at least partially enclose the heart. The excess lengths of guide strands 810 and 820 are cut with endoscopic scissors (not shown) to complete the procedure.

Figure 10A:
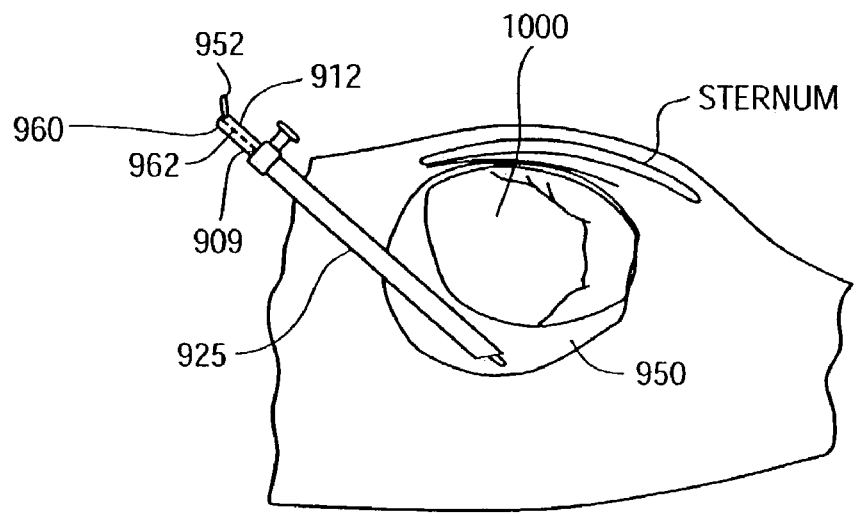
FIGS. 10A through 10C are partial cross sectional views of the operation of an endoscopic cannula and the use of an alternative embodiment of a cardiac restraint apparatus according to the present invention.
Figure 10B:
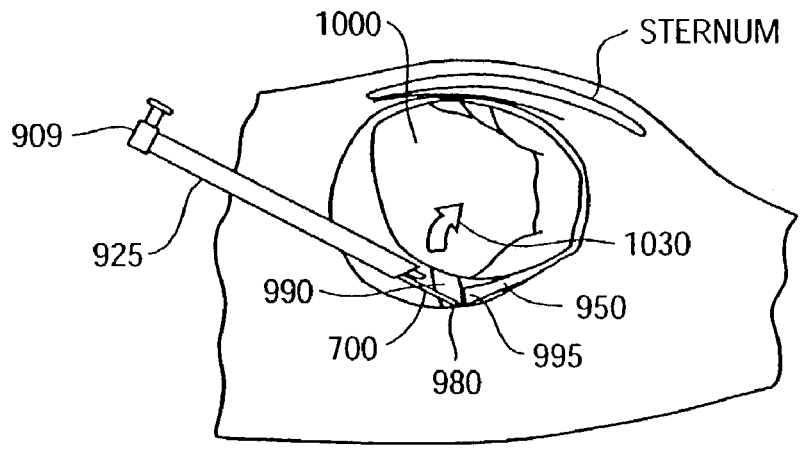
Figure 10C:
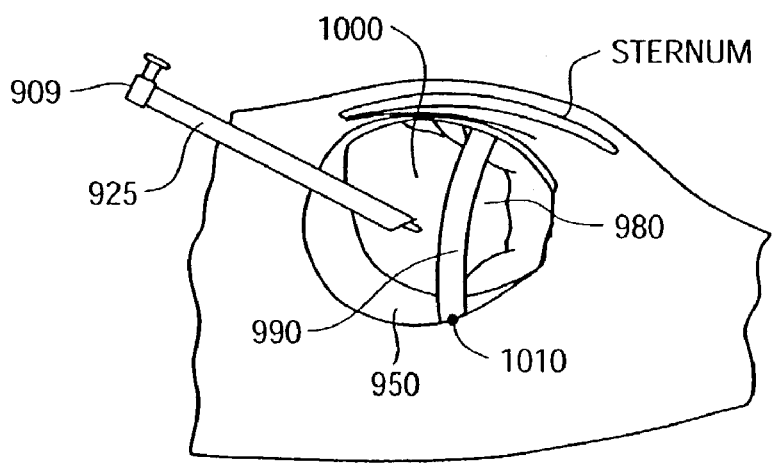

Another alternative embodiment of the method uses an alternative embodiment of a cardiac restraint apparatus according to this invention, described above and illustrated in FIGS. 9A–9B. One embodiment of this method, illustrated in FIGS. 10A–10C, is performed using the subxiphoid access method described above. Referring now to FIG. 10A, endoscopic cannula 925 is introduced into the pericardium as previously described. Cardiac restraint apparatus 960, described above with reference to FIGS. 9A–9B, is then introduced into access port 909 and into pericardium 950 via an opening made in the pericardium as previously described. The introduction of cardiac restraint apparatus 960 into the pericardium may be optionally facilitated using a rod (not shown) which pushes cardiac restraint apparatus 960 into the pericardium. Sheath 962 is then removed by pulling pull tab 952 which causes the tearing of sheath 962 along perforations 912, releasing elastic band 980 (not shown) housed within sheath 962.

Next, referring to FIG. 10B, tacking instrument 700 is introduced into the pericardium through access port 909. Tacking instrument 700 is then used to tack elastic band 980 (shown in detail in FIG. 9A) to the posterior pericardium. Preferably, elastic band 980 is tacked to the pericardium at a point located between first portion 990 and second portion 995. Alternatively, elastic band 980 is tacked to the pericardium at any point located between first end 992 and second end 996, which are not visible in the figure. Elastic band 980 can also be attached initially to the tack of the tacking instrument 700, prior to introduction of both elastic band 980 and tacking instrument 700 together through access port 909.

Next, as shown in FIGS. 10B and 10C, first portion 990 and second portion 995 of elastic band 980 (more clearly shown in FIG. 9A) are moved from the posterior pericardium to the anterior aspect of the heart, and are tacked to the pericardium overlying the heart, preferably to the anterior aspect of the heart. First portion 990 is moved to the anterior aspect of the heart in the direction of arrow 1030 by advancing a grasping instrument (not shown), for example a clip applier, into the pericardium via endoscopic cannula 925, grasping first portion 990 of elastic band 980, first portion 990 of elastic band 980 from the posterior pericardium to the anterior aspect of the heart in the direction of arrow 1030. Optionally, elastic band 980 is configured to receive a grasping instrument, for example by including openings 990 and 991 as shown in FIG. 9A. Second portion 995 is moved in the opposite direction, around the posterior aspect of the heart and over to the anterior aspect of the heart. First portion 990 and second portion 995 are then tacked to the pericardium overlying the heart. The first portion 990 and second portion 995 can be tacked or clipped together to complete the procedure.

While this method has been described with reference to a subxiphoid approach using an endoscopic cannula, the invention also contemplates methods in which the surgical incision is a subxiphoid incision, a trans-xiphoid incision, and a thorascopic incision, with or without the usage of an endoscopic cannula. In addition, the invention contemplates the use of one or more elastic bands of varying widths, preferably using three elastic bands each having a width of 1 cm.

Although the invention has been described in connection with specific preferred embodiments, various modifications and variations of the described methods and compositions of the invention will be apparent to those skilled in the art without departing from the scope and spirit of the invention.

What is claimed is:

1. A method for constraining expansion of the heart comprising the steps for:
   forming a subxiphoid entry incision;
   introducing through the subxiphoid entry incision an endoscopic cannula having at least one lumen extending therethrough;

advancing the endoscopic cannula toward the pericardium;

introducing through a lumen of the endoscopic cannula a pericardial entry instrument to form an aperture near the apical pericardium into the intrapericardial space about the heart;

advancing the endoscopic cannula through the aperture;

introducing cardiac restraint apparatus through a lumen of the endoscopic cannula into engagement with the heart; and manipulating the cardiac restraint apparatus within the intrapericardial space into substantially surrounding engagement about at least a portion of the heart.

2. The method according to claim 1 in which advancing the endoscopic cannula includes dissecting the linea alba and forming a passage posterior to the sternum toward the apex of the heart.

3. The method according to claim 1 in which introducing the cardiac restraint apparatus includes configuring the cardiac restraint apparatus within a volume dimensioned to pass through a lumen within the endoscopic cannula and through the pericardial aperture into the intrapericardial space about the heart.

4. The method according to claim 3 in which manipulating the cardiac restraint apparatus includes expanding within the intrapericardial space the cardiac restraint apparatus from the confined configuration thereof for positioning the unconfined cardiac restraint apparatus about a portion of the heart within the intrapericardial space.

5. The method according to claim 4 in which the cardiac restraint apparatus includes a jacket having a rim defining an opening for receiving a heart and including attached to the rim at least one guide handle of sufficient length to extend from the heart out through the subxiphoid entry incision, the jacket and rim and guide handle being configured within the dimension to pass through a lumen of the endoscopic cannula, and the method further comprising the step for:

positioning the rim of the jacket substantially about the heart within the intrapericardial space in response to manual manipulation of the guide handle from outside the subxiphoid entry incision.

6. The method according to claim 5 further comprising the steps for:

selectively tightening the rim about the heart; and detaching the guide handle from the rim for removal of the guide handle through the lumen of the endoscopic cannula.

7. The method according to claim 4 in which the cardiac restraint apparatus includes an elastic band for encircling the heart, the method further comprising the steps for:

introducing the elastic band through the lumen of the endoscopic cannula into the intrapericardial space; and positing the elastic band substantially encircling the heart.

* * * * *

UNITED STATES PATENT AND TRADEMARK OFFICE
CERTIFICATE OF CORRECTION

| | |
|---|---|
| PATENT NO. | : 7,214,180 B2 |
| APPLICATION NO. | : 10/338163 |
| DATED | : May 8, 2007 |
| INVENTOR(S) | : Albert K. Chin |

Page 1 of 1

It is certified that error appears in the above-identified patent and that said Letters Patent is hereby corrected as shown below:

Page 3, under "OTHER PUBLICATIONS", please insert -- BERNHARD, Victor M. et al., "Cardiovascular Endoscopy: Historical Perspectives", Endovascular Surgery, 1989 W.B. Saunders Company, pp. 13-30 --.

Claim 7, Column 16, Line 24, please delete "positing" and insert -- positioning --.

Signed and Sealed this

Seventh Day of August, 2007

JON W. DUDAS
*Director of the United States Patent and Trademark Office*